(12) United States Patent
Walling et al.

(10) Patent No.: US 11,660,445 B2
(45) Date of Patent: May 30, 2023

(54) ELECTRODE ARRAY PACKAGING SYSTEM

(71) Applicant: Cochlear Limited, Macquarie University (AU)

(72) Inventors: Grahame Michael David Walling, Macquarie University (AU); Charles Roger Aaron Leigh, Macquarie University (AU)

(73) Assignee: Cochlear Limited, Macquarie University (AU)

( * ) Notice: Subject to any disclaimer, the term of this patent is extended or adjusted under 35 U.S.C. 154(b) by 1600 days.

(21) Appl. No.: 15/164,789

(22) Filed: May 25, 2016

(65) Prior Publication Data
US 2017/0080211 A1    Mar. 23, 2017

Related U.S. Application Data

(60) Provisional application No. 62/222,271, filed on Sep. 23, 2015.

(51) Int. Cl.
*A61N 1/05*    (2006.01)
*A61F 2/00*    (2006.01)
*A61N 1/372*    (2006.01)

(52) U.S. Cl.
CPC .......... *A61N 1/0541* (2013.01); *A61F 2/0095* (2013.01); *A61N 2001/37294* (2013.01)

(58) Field of Classification Search
CPC ............................ A61N 1/0541; A61F 2/0095
See application file for complete search history.

(56) References Cited

U.S. PATENT DOCUMENTS

| | | | |
|---|---|---|---|
| 4,423,732 A * | 1/1984 | Tarjan | A61N 1/3752 206/438 |
| 4,522,209 A | 6/1985 | Patrick et al. | |
| 5,237,991 A | 8/1993 | Baker, Jr. et al. | |
| 5,579,919 A | 12/1996 | Gilman et al. | |
| 5,817,151 A * | 10/1998 | Olson | A61N 1/3931 607/142 |
| 5,957,958 A | 9/1999 | Schulman et al. | |
| 6,116,413 A | 9/2000 | Tabor et al. | |
| 6,292,697 B1 * | 9/2001 | Roberts | A61N 1/3706 607/27 |
| 7,766,905 B2 | 8/2010 | Paterson et al. | |
| 2003/0055478 A1 * | 3/2003 | Lyster | A61N 1/046 607/142 |
| 2004/0116995 A1 * | 6/2004 | Dadd | A61N 1/0541 607/137 |

(Continued)

FOREIGN PATENT DOCUMENTS

| | | |
|---|---|---|
| EP | 1959856 | 4/2013 |
| GB | 2358934 | 11/2003 |

OTHER PUBLICATIONS

International Search Report and Written Opinion for PCT/IB2016/055670, dated Dec. 8, 2016.

*Primary Examiner* — Rex R Holmes
*Assistant Examiner* — Jennifer L Ghand
(74) *Attorney, Agent, or Firm* — Pilloff Passino & Cosenza LLP; Martin J. Cosenza

(57) ABSTRACT

An apparatus, including a sterilely sealed package, and an electrode assembly sterilely sealed in the package, wherein the apparatus is configured to enable testing for an open circuit between two electrodes of the electrode assembly with the electrode assembly sterilely sealed in the package.

32 Claims, 40 Drawing Sheets

(56) References Cited

U.S. PATENT DOCUMENTS

2015/0142073 A1* 5/2015 Taff .................. B65B 55/02
607/36
2017/0056646 A1* 3/2017 Sibary ................ A61N 1/0541

* cited by examiner

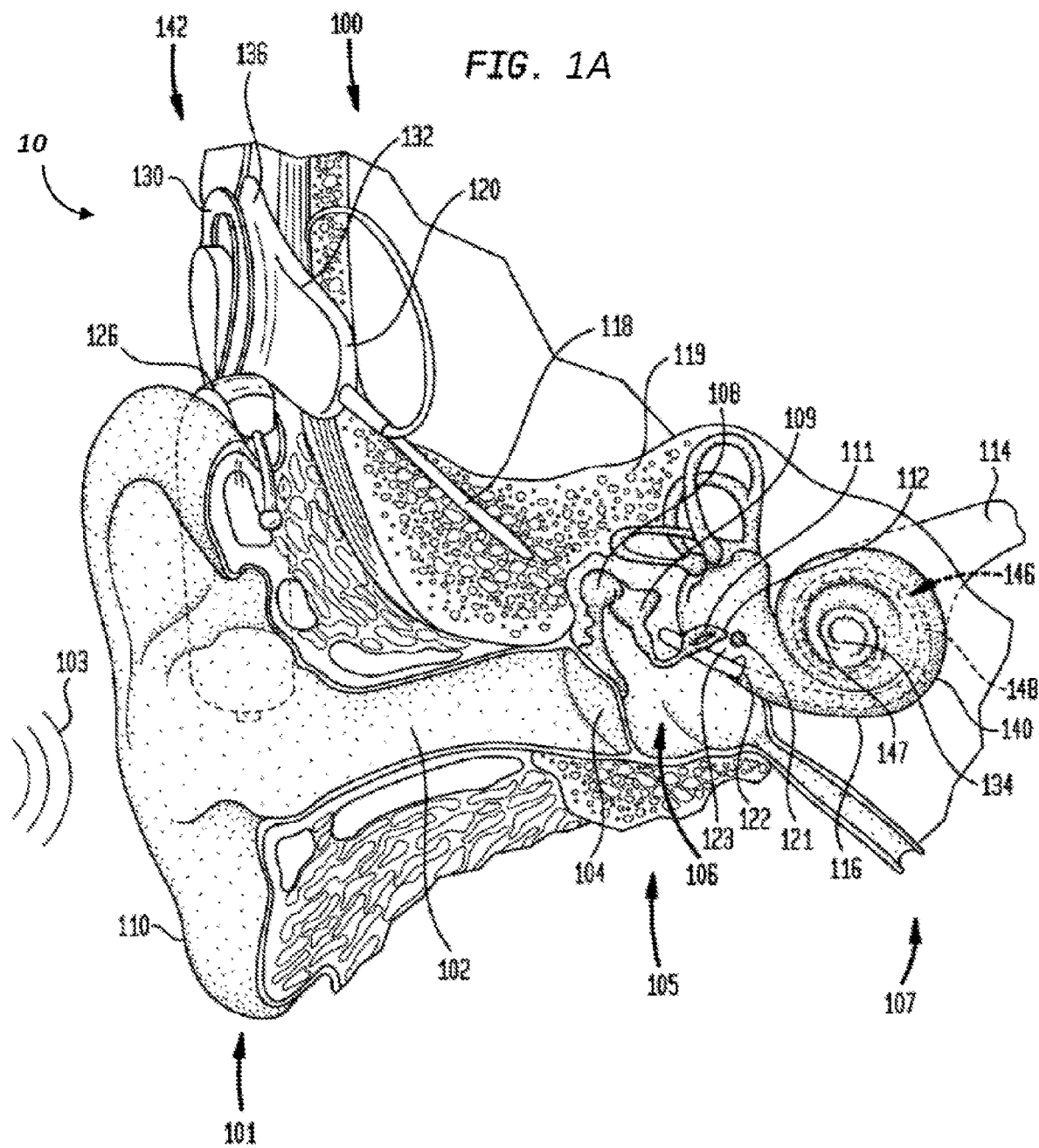

ELECTRODE ARRAY PACKAGING SYSTEM

CROSS-REFERENCE TO RELATED APPLICATIONS

This application claims priority to U.S. Provisional Patent Application No. 62/222,271, entitled ELECTRODE ARRAY PACKAGING SYSTEM, filed on Sep. 23, 2015, naming Grahame Michael David WALLING of Macquarie University, Australia as an inventor, the entire contents of that application being incorporated herein by reference in its entirety.

BACKGROUND

Hearing loss, which may be due to many different causes, is generally of two types: conductive and sensorineural. Sensorineural hearing loss is due to the absence or destruction of the hair cells in the cochlea that transduce sound signals into nerve impulses. Various hearing prostheses are commercially available to provide individuals suffering from sensorineural hearing loss with the ability to perceive sound. One example of a hearing prosthesis is a cochlear implant.

Conductive hearing loss occurs when the normal mechanical pathways that provide sound to hair cells in the cochlea are impeded, for example, by damage to the ossicular chain or the ear canal. Individuals suffering from conductive hearing loss may retain some form of residual hearing because the hair cells in the cochlea may remain undamaged.

Individuals suffering from conductive hearing loss typically receive an acoustic hearing aid. Hearing aids rely on principles of air conduction to transmit acoustic signals to the cochlea. In particular, a hearing aid typically uses an arrangement positioned in the recipient's ear canal or on the outer ear to amplify a sound received by the outer ear of the recipient. This amplified sound reaches the cochlea causing motion of the perilymph and stimulation of the auditory nerve.

In contrast to hearing aids, which rely primarily on the principles of air conduction, certain types of hearing prostheses commonly referred to as cochlear implants convert a received sound into electrical stimulation. The electrical stimulation is applied to the cochlea, which results in the perception of the received sound.

SUMMARY

In an exemplary embodiment, there is an apparatus, comprising a sterilely sealed package, and an electrode assembly sterilely sealed in the package, wherein the apparatus is configured to enable testing for an open circuit between two electrodes of the electrode assembly with the electrode assembly sterilely sealed in the package.

In another exemplary embodiment, there is a method, comprising the actions of obtaining an electrode array sterilely isolated from an external environment thereof, and testing for an open circuit between two electrodes of the electrode array while the electrode array is sterilely sealed from the external environment.

In another exemplary embodiment, there is an apparatus, comprising a package; and an electrode array sterilely sealed in the package, wherein the apparatus is configured to provide electrical conductivity between two electrodes of the electrode array.

In another exemplary embodiment, there is a system, comprising, a package and a cochlear implant comprising an electrode array and a receiver-stimulator sealed within the package, wherein the system is configured to enable two types of conductivity testing of the electrode array.

BRIEF DESCRIPTION OF THE DRAWINGS

Embodiments of the present invention are described below with reference to the attached drawings, in which:

FIG. 1A is a perspective view of an exemplary hearing prosthesis utilized in some exemplary embodiments;

DETAILED DESCRIPTION

Figure 1B:
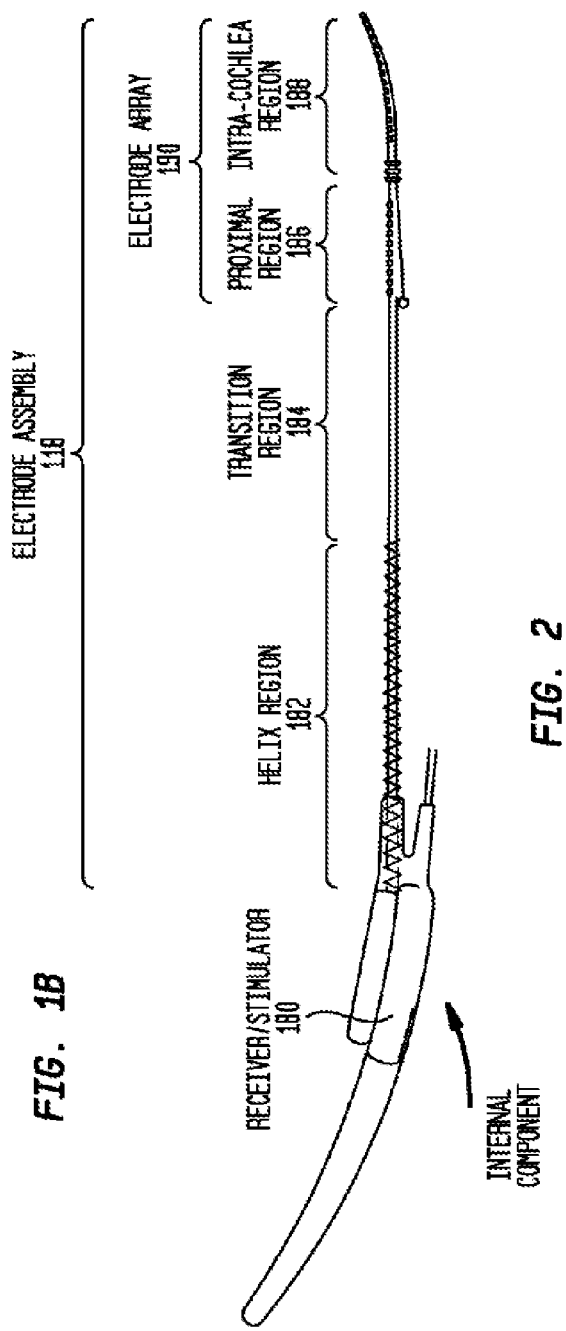
FIG. 1B is a side view of the implantable components of the cochlear implant illustrated in FIG. 1A.

FIG. 1A is a perspective view of a totally implantable cochlear implant according to an exemplary embodiment, referred to as cochlear implant 100, implanted in a recipient. The totally implantable cochlear implant 100 is part of a system 10 that can include external components, as will be detailed below.

In an alternate embodiment, the cochlear implant system is not a totally implantable system. By way of example, the cochlear implant system includes an external component that includes a microphone and a sound processor. The sound processor processes signals from the microphone, and generates a signal that is transmitted transcutaneously to an implantable component which then uses the signal to stimulate tissue and evoke a hearing percept.

It is noted that in some conventional parlances, the entire system 10 is referred to as a cochlear implant, especially in the case of a cochlear implant that is not totally implantable. Herein, the phrase cochlear implant refers to the implantable component, and the phrase cochlear implant system refers to the entire system 10. That is, the phrase cochlear implant corresponds to the implantable component of a non-totally implantable cochlear implant system.

The recipient has an outer ear 101, a middle ear 105 and an inner ear 107. Components of outer ear 101, middle ear 105 and inner ear 107 are described below, followed by a description of cochlear implant 100.

In a fully functional ear, outer ear 101 comprises an auricle 110 and an ear canal 102. An acoustic pressure or sound wave 103 is collected by auricle 110 and channeled into and through ear canal 102. Disposed across the distal end of ear canal 102 is a tympanic membrane 104 which vibrates in response to sound wave 103. This vibration is coupled to oval window or fenestra ovalis 112 through three bones of middle ear 105, collectively referred to as the ossicles 106 and comprising the malleus 108, the incus 109 and the stapes 111. Bones 108, 109, and 111 of middle ear 105 serve to filter and amplify sound wave 103, causing oval window 112 to articulate, or vibrate in response to vibration of tympanic membrane 104. This vibration sets up waves of fluid motion of the perilymph within cochlea 140. Such fluid motion, in turn, activates tiny hair cells (not shown) inside of cochlea 140. Activation of the hair cells causes appropriate nerve impulses to be generated and transferred through the spiral ganglion cells (not shown) and auditory nerve 114 to the brain (also not shown) where they are perceived as sound.

As shown, cochlear implant 100 comprises one or more components which are temporarily or permanently implanted in the recipient. Cochlear implant 100 is shown in FIG. 1A with an external device 142, that is part of system 10 (along with cochlear implant 100), which, as described below, is configured to provide power to the cochlear implant.

In the illustrative arrangement of FIG. 1A, external device 142 may comprise a power source (not shown) disposed in a Behind-The-Ear (BTE) unit 126. External device 142 also includes components of a transcutaneous energy transfer link, referred to as an external energy transfer assembly. The transcutaneous energy transfer link is used to transfer power and/or data to cochlear implant 100. Various types of energy transfer, such as infrared (IR), electromagnetic, capacitive and inductive transfer, may be used to transfer the power and/or data from external device 142 to cochlear implant 100. In the illustrative embodiments of FIG. 1, the external energy transfer assembly comprises an external coil 130 that forms part of an inductive radio frequency (RF) communication link. External coil 130 is typically a wire antenna coil comprised of multiple turns of electrically insulated single-strand/or multi-strand platinum or gold wire. External device 142 also includes a magnet (not shown) positioned within the turns of wire of external coil 130. It should be appreciated that the external device shown in FIG. 1 is merely illustrative, and other external devices may be used with embodiments of the present invention.

Cochlear implant 100 comprises an internal energy transfer assembly 132 which may be positioned in a recess of the temporal bone adjacent auricle 110 of the recipient. As detailed below, internal energy transfer assembly 132 is a component of the transcutaneous energy transfer link and receives power and/or data from external device 142. In the illustrative embodiment, the energy transfer link comprises an inductive RF link, and internal energy transfer assembly 132 comprises a primary internal coil 136. Internal coil 136 is typically a wire antenna coil comprised of multiple turns of electrically insulated single-strand/or multi-strand platinum or gold wire.

Cochlear implant 100 further comprises a main implantable component 120 and an elongate stimulating assembly 118. In embodiments of the present invention, internal energy transfer assembly 132 and main implantable component 120 are hermetically sealed within a biocompatible housing. In embodiments of the present invention, main implantable component 120 includes a sound processing unit (not shown) to convert the sound signals received by the implantable microphone in internal energy transfer assembly 132 to data signals. Main implantable component 120 further includes a stimulator unit (also not shown) which generates electrical stimulation signals based on the data signals. The electrical stimulation signals are delivered to the recipient via elongate stimulating assembly 118.

Elongate stimulating assembly 118 has a proximal end connected to main implantable component 120, and a distal end implanted in cochlea 140. Stimulating assembly 118 extends from main implantable component 120 to cochlea 140 through mastoid bone 119. In some embodiments stimulating assembly 118 may be implanted at least in basal region 116, and sometimes further. For example, stimulating assembly 118 may extend towards apical end of cochlea 140, referred to as cochlea apex 134. In certain circumstances, stimulating assembly 118 may be inserted into cochlea 140 via a cochleostomy 122. In other circumstances, a cochleostomy may be formed through round window 121, oval window 112, the promontory 123 or through an apical turn 147 of cochlea 140.

Stimulating assembly 118 comprises a longitudinally aligned and distally extending array 146 of electrodes 148, disposed along a length thereof. As noted, a stimulator unit generates stimulation signals which are applied by stimulating contacts 148, which, in an exemplary embodiment, are electrodes, to cochlea 140, thereby stimulating auditory nerve 114. In an exemplary embodiment, stimulation contacts can be any type of component that stimulates the cochlea (e.g., mechanical components, such as piezoelectric devices that move or vibrate, thus stimulating the cochlea (e.g., by inducing movement of the fluid in the cochlea), electrodes that apply current to the cochlea, etc.). Embodiments detailed herein will generally be described in terms of an electrode assembly 118 utilizing electrodes as elements 148. It is noted that alternate embodiments can utilize other types of stimulating devices. Any device, system or method of stimulating the cochlea can be utilized in at least some embodiments.

As noted, cochlear implant 100 comprises a totally implantable prosthesis that is capable of operating, at least for a period of time, without the need for external device 142. Therefore, cochlear implant 100 further comprises a rechargeable power source (not shown) that stores power received from external device 142. The power source may comprise, for example, a rechargeable battery. During operation of cochlear implant 100, the power stored by the power source is distributed to the various other implanted components as needed. The power source may be located in main implantable component 120, or disposed in a separate implanted location.

It is noted that the teachings detailed herein and/or variations thereof can be utilized with a non-totally implantable prosthesis. That is, in an alternate embodiment of the cochlear implant 100, the cochlear implant 100 is a traditional hearing prosthesis.

While various aspects of the present invention are described with reference to a cochlear implant (whether it be a device utilizing electrodes or stimulating contacts that impart vibration and/or mechanical fluid movement within the cochlea), it will be understood that various aspects of the embodiments detailed herein are equally applicable to other stimulating medical devices having an array of electrical simulating electrodes such as auditory brain implant (ABI), functional electrical stimulation (FES), spinal cord stimulation (SCS), penetrating ABI electrodes (PABI), and so on. Further, it should be appreciated that the present invention is applicable to stimulating medical devices having electrical stimulating electrodes of all types such as straight electrodes, peri-modiolar electrodes and short/basilar electrodes. Also, various aspects of the embodiments detailed herein and/or variations thereof are applicable to devices that are non-stimulating and/or have functionality different from stimulating tissue, such as for, example, any intra-body dynamic phenomenon (e.g., pressure, or other phenomenon consistent with the teachings detailed herein) measurement/sensing, etc., which can include use of these teachings to sense or otherwise detect a phenomenon at a location other than the cochlea (e.g., within a cavity containing the brain, the heart, etc.). Additional embodiments are applicable to bone conduction devices, Direct Acoustic Cochlear Stimulators/Middle Ear Prostheses, and conventional acoustic hearing aids. Any device, system or method of evoking a hearing percept can be used in conjunction with the teachings detailed herein.

FIG. 1B is a side view of the internal component of cochlear implant 100 without the other components of system 10 (e.g., the external components). Cochlear implant 100 comprises a receiver/stimulator 180 (combination of main implantable component 120 and internal energy transfer assembly 132) and a stimulating assembly or lead 118. Stimulating assembly 118 includes a helix region 182, a transition region 184, a proximal region 186, and an intra-cochlear region 188. Proximal region 186 and intra-cochlear region 188 form an electrode array assembly 190. In an exemplary embodiment, proximal region 186 is located in the middle-ear cavity of the recipient after implantation of the intra-cochlear region 188 into the cochlea. Thus, proximal region 186 corresponds to a middle-ear cavity subsection of the electrode array assembly 190. Electrode array assembly 190, and in particular, intra-cochlear region 188 of electrode array assembly 190, supports a plurality of electrode contacts 148. These electrode contacts 148 are each connected to a respective conductive pathway, such as wires, PCB traces, etc. (not shown) which are connected through lead 118 to receiver/stimulator 180, through which respective stimulating electrical signals for each electrode contact 148 travel.

Figure 2:
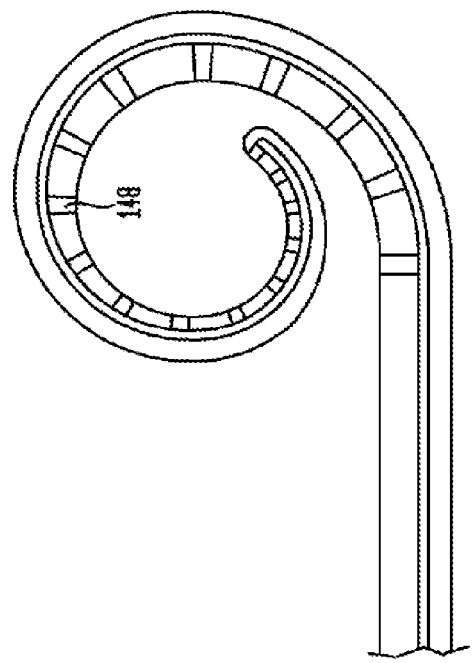
FIG. 2 is a side view of an embodiment of the electrode array illustrated in FIGS. 1A and 1B in a curled orientation.

FIG. 2 is a side view of electrode array assembly 190 in a curled orientation, as it would be when inserted in a recipient's cochlea, with electrode contacts 148 located on the inside of the curve. FIG. 2 depicts the electrode array of FIG. 1B in situ in a patient's cochlea 140.

Figure 3:
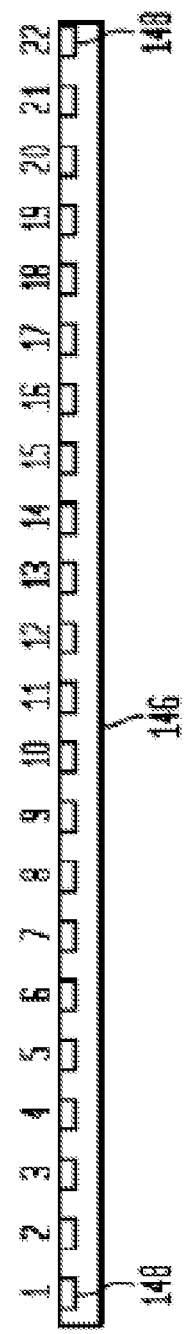
FIG. 3 is a functional schematic of an electrode array including 22 electrodes spaced apart from one another.

FIG. 3 illustrates a more detailed view, albeit functionally, of an exemplary electrode array 146 comprising a plurality of electrodes 148 labeled 1-22, in accordance with an embodiment. In an exemplary embodiment, each electrode 148 is an electrode that corresponds to a specific frequency band channel of the cochlear implant 100, where electrode 22 corresponds to the lowest frequency band (channel), and electrode 1 corresponds to the highest frequency band (channel) as will be discussed in greater detail below. Briefly, it is noted that during stimulation by the electrodes to evoke a hearing percept, one or more electrodes 148 is activated at a given electrode stimulation level (e.g., current level).

There is utilitarian value in a structure of a cochlear implant where one or more of the electrodes 148 is electrically isolated from one or more other electrodes 148 (e.g., current does not flow from one electrode to another electrode when the cochlear implant 100, or at least the array 190, is isolated from a conductive media that is not part of the cochlear implant 100, at least not unless the cochlear implant is configured to alternately enable such flow, in which case there is utilitarian value in a structure that can alternately prevent such flow from occurring). Corollary to this is that there is utilitarian value in a structure of a cochlear implant where one or more of the electrodes 148 are in electrical conductivity with the receiver/stimulator 180 (e.g., current flows from the receiver/stimulator 182 one or more of the electrodes 148, which, in an exemplary embodiment, the current flows through the electrode assembly 118 from the receiver/stimulator 180).

In at least some exemplary embodiments, there is utilitarian value in testing for shorts and/or opens with respect to the electrode assembly 118. In at least some exemplary embodiments, a short is detected as a low impedance between two or more electrodes 148. In at least some exemplary embodiments, an open is detected as a high impedance between a given electrode 148 and another electrode (whether the another electrode be on the same electrode array as the given electrode, or on a separate component (e.g., the extra-cochlear electrode on another lead, an electrode on the receiver stimulator, etc.) and/or between a given electrode 148 and the receiver/stimulator 180.

In an exemplary embodiment, a test for an open entails making an electrical connection to the electrode 148 under test. In an exemplary embodiment, a test for a closed entails energizing one electrode 148 and testing for an electrical current at one of the other electrodes 148.

In at least some exemplary embodiments, the cochlear implant 100, or at least the electrode array assembly 190, is shipped in a sterilely sealed sterile package. According to some exemplary embodiments, there is utilitarian value in testing for opens and shorts while the cochlear implant 100 in general, and the electrode array assembly 190, remains sterilely sealed in the sterile package. In at least some exemplary embodiments, this can enable testing for opens and shorts without exposing the cochlear implant 100, or at least the electrode array assembly 190, to a nonsterile environment. In an exemplary embodiment, this can entail detecting for an open and/or a short circuit without opening the package, and enabling the cochlear implant 100 to be returned to the manufacturer in a sterile environment (because the packaging was never opened) upon a determination that there exist in open and/or a short.

Figure 4:
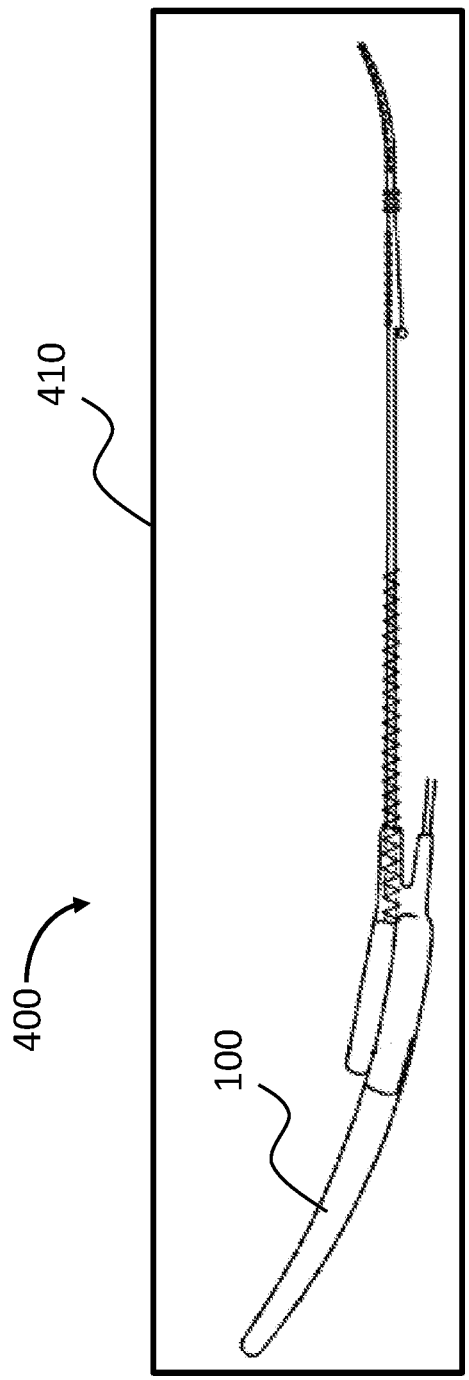
FIG. 4 is a schematic of an apparatus according to an exemplary embodiment.

FIG. 4 presents a functional schematic of an exemplary embodiment of the cochlear implant 100 in such a package. Specifically, there is shown an apparatus 400 including a cochlear implant 100, and thus an electrode array assembly 190, which includes an electrode array 146, sterilely sealed in package 410. The package material can be any type of package that can enable the teachings detailed herein and/or variations thereof to be practiced. In an exemplary embodiment, the packaging corresponds to the packaging used to package cochlear implants manufactured by Cochlear Ltd. of Australia. In an exemplary embodiment, the packaging from Cochlear Ltd. of Australia is at least generally unmodified, and the additional features detailed herein are added within the packaging as a separate component (albeit the packaging can have a different dimensional form to correspond to the additional components therein, such as in the case where the packaging is made of preformed plastic (as opposed to flexible plastic) the key here is that the packaging is generally the same, with the addition of additional components therein). In other exemplary embodiments, the packaging from Cochlear Ltd. of Australia is modified so that the teachings detailed herein and/or variations thereof are integral with the packaging or otherwise attached to the packaging (as opposed to being contained in the packaging).

By way of example only and not by way limitation, in an exemplary embodiment, the packaging is preformed plastic material that is configured to form a sterile seal such that the cochlear implant 100 can be stored in a sterile environment until the packaging is open. In an exemplary embodiment, the packaging corresponds to two separate portions of preformed plastic that is heat sealed to each other to form the sterile seal. Alternatively, in an exemplary embodiment, the packaging is flexible and analogous to "sandwich bag" material.

Some additional features of the packaging will be described below. Briefly, it is noted that in at least some exemplary embodiments, the package 410 is configured to enable inductance communication (or any other applicable communication format that will enable the teachings detailed herein and/or variations thereof to be practiced) with the receiver/stimulator 180 through the packaging 410. In an exemplary embodiment, the communication can correspond to the communication that transcutaneously takes place between the external component 142 and the implantable component 100 in the system 10 detailed above. That is, in an exemplary embodiment, the communication through the packaging 410 can be executed utilizing techniques that are the same as, or at least analogous to, the transcutaneous communication that takes place while the cochlear implant 100 is implanted in a recipient fully and completely beneath the skin. In at least some exemplary embodiments, the communication that takes place through the package 410 is a telemetric communication.

In an exemplary embodiment, the apparatus 400 is configured to enable testing for an open circuit between two or more electrodes of the electrode assembly 190 with the electrode assembly 190 sterilely sealed in the package. In at least some exemplary embodiments, this is achieved in part due to the aforementioned communication abilities between the receiver/stimulator 180 and the outside of the package, where a test apparatus is located (more on this below). In some exemplary embodiments, only the electrode array assembly 190 is sterilely sealed in a package. Alternatively, and/or in addition to this, another device can be located within the package 410 that can provide an indicator through the package to indicate whether or not an open circuit (and/or a short circuit for that matter) is present.

Briefly, any device, system and/or method that can enable communication through the package 410, that can enable the teachings detailed herein and/or variations thereof to be practiced, can be utilized in at least some exemplary embodiments. That said, the embodiments detailed below will typically be described in terms of the aforementioned inductance communication through the package 410.

With respect to the testing for an open circuit between two electrodes of the electrode assembly 190 with the electrode assembly 190 sterilely sealed in the package 410, in an exemplary embodiment, the package material and/or a component within the package is a sufficiently conductive material to establish sufficient electrical conduction between two separate electrodes to check for an open circuit. In an exemplary embodiment, this can have utilitarian value in that the cochlear implant 100, or at least the electrode array assembly 190, is in a state prepared for direct implantation into a recipient upon opening of the package 410. That is, in an exemplary embodiment, the electrode array assembly 190 and/or the entire cochlear implant 100 can be tested for an open circuit while the pertinent components are located in a sterile package/sterile environment without opening the package (i.e., the enclosure in which the components are located remain sterile), and then, essentially immediately after the testing (thus confirming that the electrode array assembly 190 contains no open circuits, and thus is ready for implantation at least with respect to this feature), the cochlear implant 100 and electrode array assembly 190 can be implanted in a recipient. Additional features of this concept will be described below. First, however, some exemplary features of the testing for an open circuit and/or a short circuit will now be described.

Figure 5:
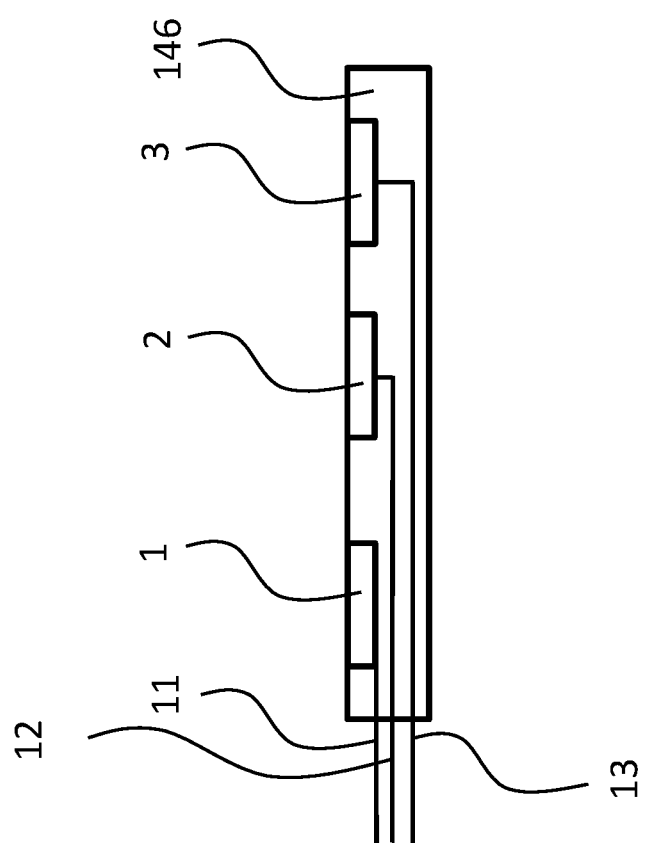
FIG. 5 is a quasi-functional schematic of an electrode array according to an exemplary embodiment.

In general terms, FIG. 5 depicts a quasi-functional diagram of a portion of electrode array 146, depicting electrodes 1, 2, and 3, which are respectively connected to leads 11, 12, and 13, which leads extend from the respective electrodes to the proximal end of the electrode array assembly 190, and then to receiver/stimulator 180. While only three electrodes and three leads are depicted in FIG. 5, it is to be understood that in at least some embodiments, more electrodes and more leads are present in electrode array 146. Indeed, with respect to FIG. 4, there are 22 electrodes and 22 leads. Only three electrodes and only three leads are depicted in FIG. 5 for clarity.

In isolation, without any contact with the package 410, or any other material for that matter, to test for a short, a source of current is applied to any one of the leads 11, 12, or 13. If current is detected (this phenomenon is described generally—in at least some exemplary embodiments, the "detection" corresponds to a given functionality of the receiver/ stimulator 180 that can be telemetrically transmitted through the packaging and analyzed—more on this below) at any one of the other leads 11, 12, and/or 13, a determination can be made that a short exists. This is because the impedance between the electrodes 11, 12, and 13 should be relatively high (the material connecting the electrodes 148 is typically made of silicone). The leads 11, 12, and 13 are insulated from one another and from the electrodes other than the respective electrodes associated with the respective leads.

Conversely, to detect for an open, in the absence of contact with the package 410 or any other component as detailed herein, because of the high impedance between the respective electrodes, and the aforementioned electrical insulation, there is nothing to close the circuit between a source of electrical current applied to one lead, and a detector (again, this is used generally—more on this below) located at any of the other leads.

Accordingly, in an exemplary embodiment, the apparatus 400 is configured to enable testing for an open circuit between two electrodes by utilizing material of the package 410 that is sufficiently conductive to test for an open circuit when placed into contact with two or more electrodes 148 of the electrode array 146. In an exemplary embodiment, the entire package 410 is made of the requisite conductive material. In an exemplary embodiment, only a portion of the package 410 is made of the requisite conductive material. By way of example only and not by way of limitation, at least the interior of the package 410 can be made of the requisite conductive material, or at least coated with the requisite material or otherwise the requisite material is attached to the interior thereof, and the exterior of the package is made from a different type of material that is not as conductive (including non-conductive/a material of a high impedance). In an exemplary embodiment, only a portion of the package is made of the requisite conductive material. For example, only the portion of the package that is located proximate or otherwise at the electrode array assembly 190 or the electrode array 146 is made of the requisite conductive material. Any arrangement that can enable the testing of an open circuit while the cochlear implant 100 generally, and the electrode array assembly 190 specifically, is sterilely isolated or otherwise sterilely sealed in a package 410 can be utilized at least some embodiments. However, as will be detailed below, in an alternate exemplary embodiment, the apparatus 400 includes a component that is separate from the packaging 410 that enables testing for an open circuit to be executed.

In an exemplary embodiment, the material of the package 410 and/or other material located within package 410 and/or the material of the component located therein that enables testing for an open circuit has a "midrange" impedance, or at least enables the establishment of a midrange impedance between two or more electrodes, such that both testing for an open circuit, and testing for a short circuit can be implemented. In other exemplary embodiments, the apparatus 400 is configured to enable the impedance between two given electrodes to be changed from an impedance that enables testing for a short circuit to an impedance that enables testing for an open circuit. Some exemplary features of these exemplary embodiments will now be described in greater detail below.

In an exemplary embodiment, the apparatus 400 is configured to provide a controlled impedance between two or more electrodes that will enable at least testing for an open circuit between two electrodes, if not both testing for an open circuit and testing for a short circuit between two electrodes.

Thus, in an exemplary embodiment, there is a system comprising a package 410 and a cochlear implant 100 comprising an electrode array 146 and a receiver/stimulator 180 sealed within the package 410. In this exemplary embodiment, the system is configured to enable two types of conductivity testing of the electrode array (e.g., testing for an open circuit and testing for a short circuit). In an exemplary embodiment, the electrode array 146, or the entire cochlear implant 100, is sterilely sealed within the package 410. In an exemplary embodiment, the system is configured maintain the electrode array 146 or the entire cochlear implant 100, in a sterilely sealed state before, during and after the two types of testing (or at least testing for an open circuit). That is, in an exemplary embodiment, testing for the open circuit and/or the short circuit can be executed while maintaining the electrode array, or even the entire cochlear implant 100, in a sterile environment. As noted herein, in an exemplary embodiment, this testing is achieved utilizing the inductance communication between the receiver/stimulator 180 of the cochlear implant 100 and the external environment, which is a nonsterile environment.

Figure 6:
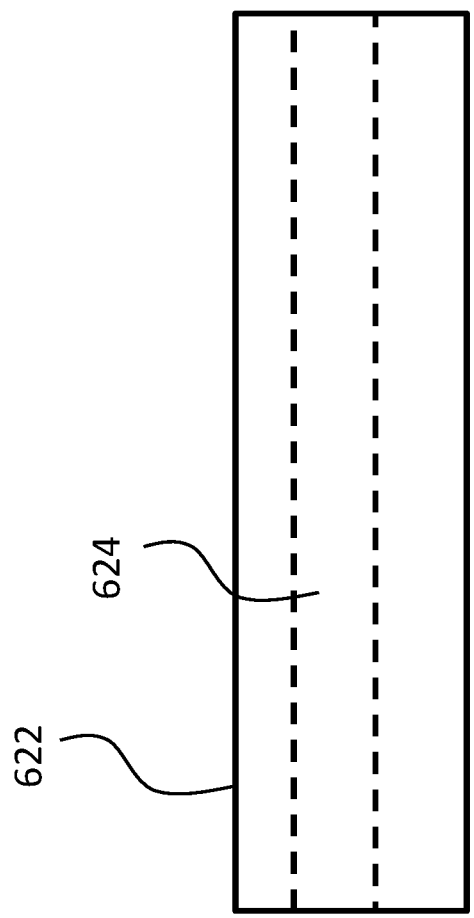
FIG. 6 is a schematic of a conductive apparatus according to an exemplary embodiment.

FIG. 6 depicts an exemplary conductive apparatus 622 in the form of an elongate cylinder having a passage 624 therethrough, wherein the passage 624 is sized and dimensioned to receive the electrode array 146 therein such that at least two electrodes of the electrode array 146 contact the interior walls of the passage 624 to establish electrical conductivity between the electrodes. In an exemplary embodiment, the conductive apparatus 622 is configured such that an impedance between any two locations on the interior surface of the passage 624 within a distance corresponding to the distance between two electrodes 148 of the electrode array 146 that will be inserted or otherwise located within passage 624 is less than about 500 ohms (or any other value that will enable testing for an open circuit between two electrodes—more on this below). In this regard, it is noted that all disclosures of impedance and related phenomenon detailed herein both correspond to the structure being described, and how the structure is arranged or otherwise used. That is, because impedance varies both with respect to distance and with respect to material type (along with some other features) and it is the resulting impedance that imparts utilitarian value on to the teachings detailed herein, as opposed to the specific impedance of a given material or the like, any disclosure herein regarding material properties also corresponds to the functionality of the resulting apparatuses when utilized according to the teachings detailed herein and/or variations thereof.

Figure 7:
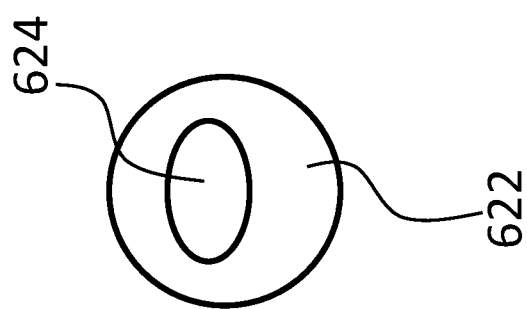
FIG. 7 is another view of the conductive apparatus of FIG. 6.

FIG. 7 depicts a view looking down the longitudinal axis of the conductive apparatus 622 (i.e. looking from the left or the right with respect to the frame of reference of FIG. 6). It is noted that the geometric shapes presented in these FIGs. are but exemplary. Any configuration that will enable the teachings detailed herein and/or variations thereof to be practiced can be utilized.

It is further noted that while the embodiment depicted in FIG. 6 and FIG. 7 is depicted as a monolithic component (in an exemplary embodiment, the entire body 622 is made from a conductive material such as gold, and thus conductive apparatus 622 is a tube or cylinder of gold), in an alternative embodiment, the conductive apparatus 622 can be a multilithic component. Indeed, in an exemplary embodiment, the walls of the passageway 624 can be coated with a conductive material (e.g., gold), and the remainder of the conductive apparatus 622 is made of a relatively nonconductive material (e.g., rubber, silicone, etc.). In this regard, for embodiments where the conductor used to test for the open circuit is movable in and out of position, the impedance rage of the conductor can be very low.

It is noted that in an exemplary embodiment, the entire body 622 and/or a portion thereof (e.g., the portion making up the walls of the passageway 624) is a conductive foam or conductive polymer. Typically this is foam or polymer containing conductive elements (e.g., loaded with silver, gold or carbon, etc.).

Figure 8:
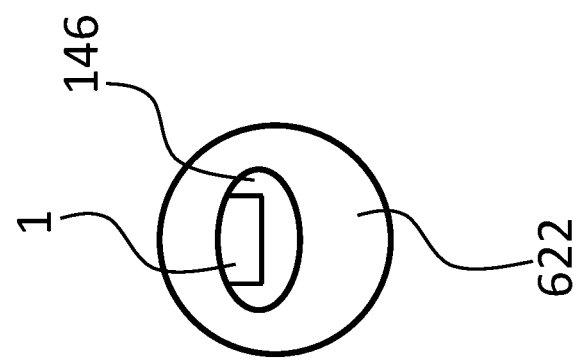
FIG. 8 depicts the view of FIG. 7, along with a cross-sectional view of an electrode array located in the conductive apparatus.
Figure 9:
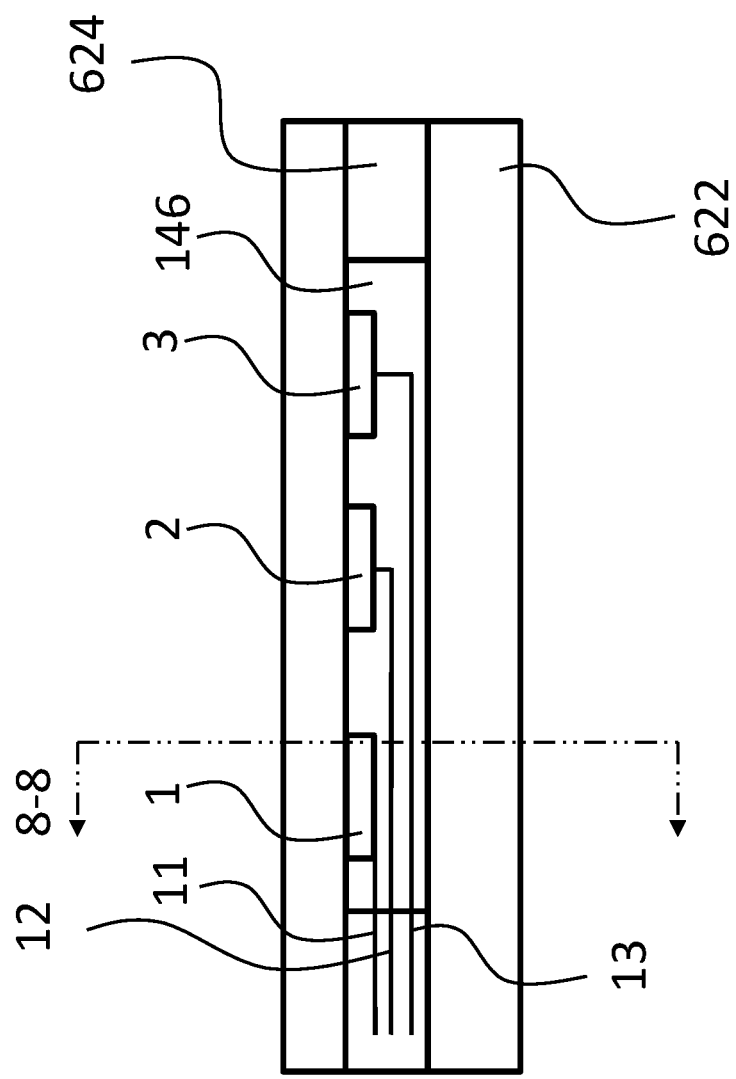
FIG. 9 depicts a side view of FIG. 8.

FIG. 8 depicts the view of FIG. 7, with the addition of the electrode array 146 being located in the passage 624 (the array is shown in cross-section). More particularly, the view of FIG. 8 depicts a cross-sectional view of an electrode array 146 taken at a location where electrode 1 is located. FIG. 9 presents FIG. 8 in greater context, which depicts a side view of a cross-section through the conductive apparatus 622 with the electrode array 146 located therein.

As can be seen, the electrodes 148 are in contact with the inner surface of the passageway 624. In this embodiment, the contact is sufficient to provide electrical conductivity from electrode 1 to electrode 2 and/or electrode 3 such that testing for an open circuit between one of these electrodes can be implemented. Corollary to this is that the conductive apparatus 622 is configured to maintain the requisite contact to enable testing for an open circuit between two or more the electrodes and/or be placed and held in that configuration for such testing to be executed. In an exemplary embodiment, conductive apparatus 622 is made of a conductive foam material, wherein an interference fit is established between the electrode array 146, and thus the electrodes 148, and the inner surface of the passage 624. In an exemplary embodiment, the interference fit ensures that sufficient contact will be made between the inner surface of the passage 624 and the respective surfaces of the electrodes 148. In an exemplary embodiment, the use of foam ensures or otherwise substantially lessens the chance that the array 146 will be damaged due to contact between the array and the conductive apparatus 622. This will be described in greater detail below.

Figure 10A:
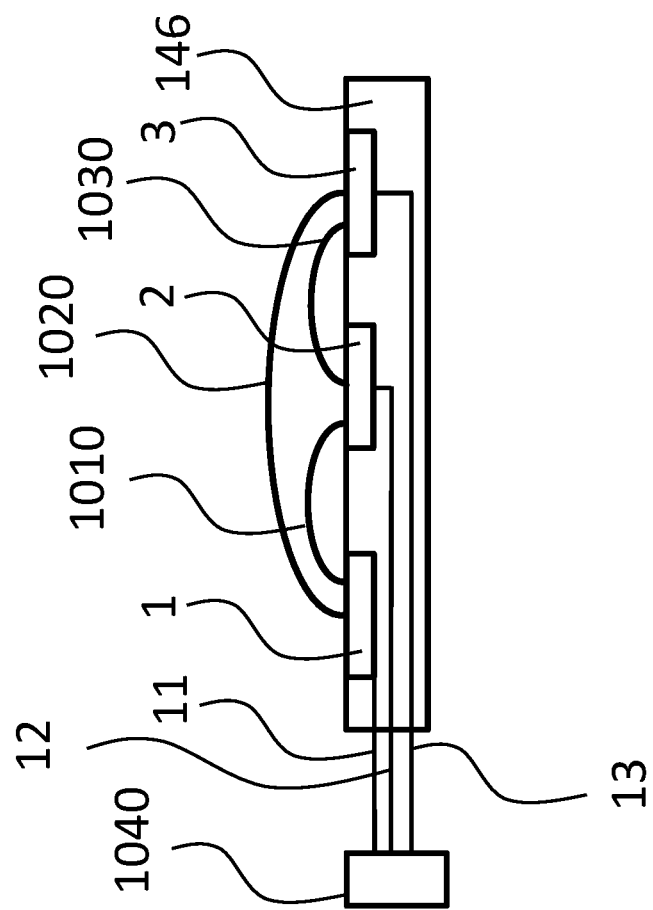
FIG. 10A depicts a functional schematic of an arrangement according to an exemplary embodiment presented for purposes of conceptual conveyance.
Figure 10B:
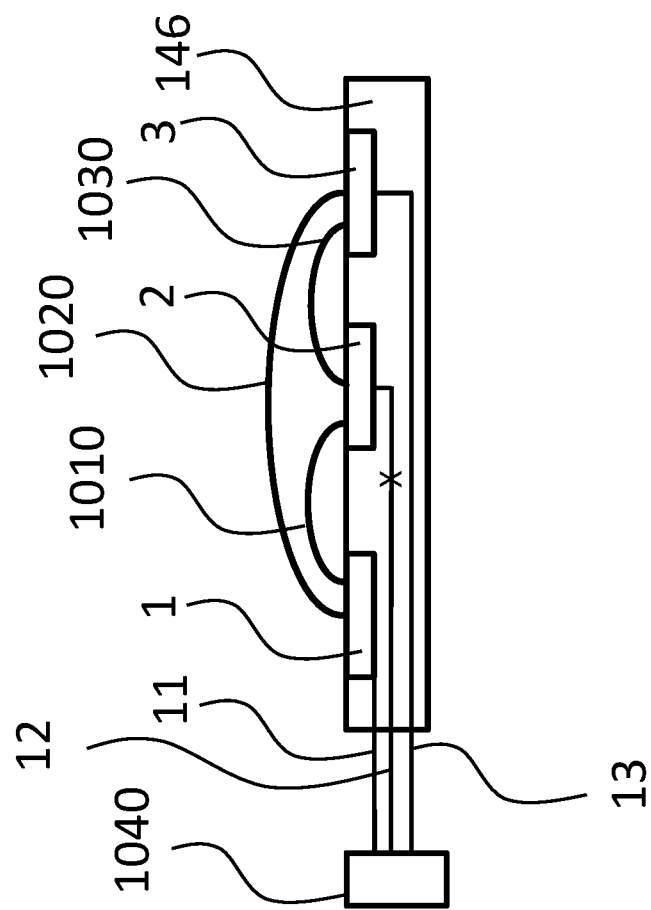
FIG. 10B depicts another functional schematic of an arrangement according to an exemplary embodiment presented for purposes of conceptual conveyance.

FIG. 10B presents a functional representation of the functionality of the conductive apparatus 622, where hypothetical leads 1010 and 1020 are located between electrodes 1 and 2 and between electrodes 1 and 3, respectively. Also shown is hypothetical lead 1030, which is located between electrodes 2 and 3. These leads place the various electrodes into electrical conductivity with one another so that testing for an open circuit can be executed. Also depicted by way of black box format is a current generator/detector 1040, which is configured to apply current to one or more of the leads 11, 12, 13, and detect a current (if there is no open circuit) at one or more of the other of leads 11, 12, 13. The current generator/detector 1040 is but a functional representation of the operation of the receiver/stimulator 180 and/or a test device located outside of the package 410 that is in communication with the cochlear implant 100 as will be detailed below. That said, in some alternate embodiments, current generator/detector 1040 can be an ohmmeter and/or a multimeter, albeit one adapted for the types of voltage and current suitable for testing of a cochlear electrode array or other array to which the teachings detailed herein are applicable.

Briefly, in an exemplary embodiment, a current is applied by current generator/detector 1040 to lead 12. Current generator/detector 1040 "looks" for a current at either or both of leads 11 and 13. Because the conductive apparatus 622 has placed electrode 2 into electrical conductivity with electrodes 1 and 3 via hypothetical leads 1010 and 1030, a current should register at one or both of leads 11 and 13 (or only one of the leads if only one of the hypothetical leads 1010 and 1030 or present) thus indicating that there is no open circuit between current generator detector 1040 and electrode 2.

Note that by "looking" for a current at two or more leads, the scenario where an open circuit exists with respect to one of the other leads, which open circuit could give a "false-negative" with respect to the lead under test can be accounted for in an exemplary embodiment. For example, if lead 12 is being tested (or, more precisely, testing for an open circuit is being performed between current generator/detector 1040 and electrode 2), and if only one lead, such as lead 11, was being utilized for the test, failure to detect a current by current generator/detector 1040 at lead 11 would not necessarily indicate a break for an open circuit associated with lead 12. This is because lead 11 could have failed. However, if a current is detected at lead 13 but not lead 11, it can be surmised that lead 12 is in proper working order, and lead 11 has experienced a failure mode. That is, it can be extrapolated or otherwise inferred that lead 11 has failed in some matter (i.e., the open circuit is between current generator/detector 1040 and electrode 1). In this regard, exemplary embodiments include algorithms to more quickly test a plurality of circuits in view of the fact that deductive logic can be utilized when more than two electrodes are placed into electrical conductivity with one another via conductive apparatus 622.

Note further that to test for a short circuit, the hypothetical leads are removed from the electrodes (e.g., the conductive apparatus 622 is pulled away from the electrode assembly 146). A current is applied to one or more of the leads, and current is looked for at one or more of the other leads. No current (or only specific current—more on this below) should be detected because the hypothetical leads have been removed. Still further, in an exemplary embodiment, the material of the package 410 has a sufficiently low conductivity (sufficiently high impedance). Thus, even if the package 410 is in contact with the electrodes, little to no current should register on the other leads.

FIG. 10B presents a hypothetical open circuit scenario, where lead 12 has experienced a break at the location indicated by the "X." In an exemplary method, a current is applied by current generator/detector 1040 to lead 12. Current generator/detector 1040 "looks" for a current at either or both of leads 11 and 13. Because the conductive apparatus 622 has placed electrode 2 into electrical conductivity with electrodes 1 and 3 via hypothetical leads 1010 and 1030, a current will not register at either of leads 11 and 13 (or only one of the leads if only one of the hypothetical leads 1010 and 1030 or present) thus indicating that there is an open circuit, must likely between current generator detector 1040 and electrode 2.

Note that by "looking" for a current at two or more leads, it can be immediately deduced that there is a fault between current generator/detector 1040 and electrode 2 (or a simultaneous fault in electrodes 1 and 3, which can be addressed by running the test by applying current at lead 11 and/or lead 13 and looking at lead 12).

Note further that in at least some exemplary methods, the methods are not executed to detect which lead or which connection is open or otherwise has experienced a failure mode. A determination that there is some failure anywhere will typically be utilitarian in that a determination can be made in view of the single failure detection that the cochlear implant 100 should not be implanted in the recipient at that time. In an exemplary embodiment, a new cochlear implant 100, such as a cochlear implant 100 located in a new apparatus 400, will be obtained, and a new round of testing for an open circuit will be executed. Such is also the case with respect to detecting which particular electrodes are associated with a short circuit.

Note that by way of example only and not by way of limitation, in an exemplary embodiment, a failure mode can correspond to a break in a lead and/or a disconnect between a lead and an electrode, which failure mode can typically results in an open circuit. In an exemplary embodiment, this can occur during shipping of the apparatus 400. In an exemplary embodiment, this can also occur during handling of the apparatus 400 prior to opening the packaging 410.

Figure 11:
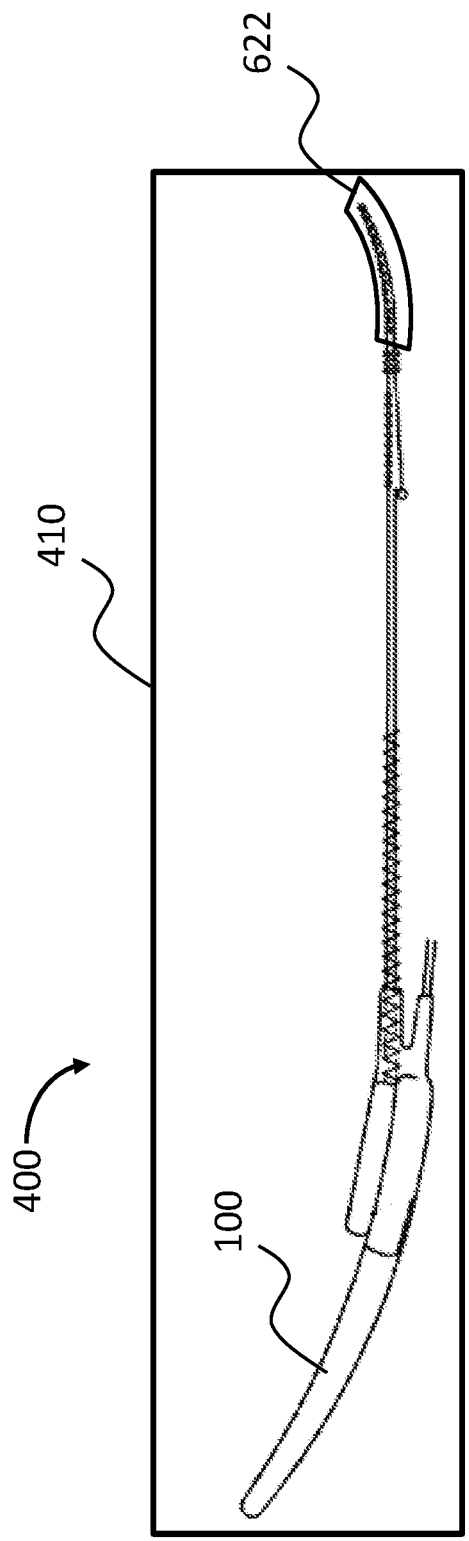
FIG. 11 is a schematic of another example of an apparatus according to an exemplary embodiment.

FIG. 11 depicts an exemplary apparatus 400, including the cochlear implant 100 and the conductive apparatus 622 located in package 410, where the electrode array 146 is located within the passage of the conductive apparatus 622 such that testing for an open circuit can be executed according to the teachings detailed herein. As can be seen, conductive apparatus 622 is presented in a curved state so as to conform to curved electrode array 146. In an exemplary embodiment, conductive apparatus 622 is rigid, and is curved in a manner that corresponds to the curvature of the curved electrode array 146. In an alternate embodiment, conductive apparatus 622 is flexible so that it flexes or otherwise can be curved to conform to the curve of the electrode array 146. Note further that in an exemplary embodiment, conductive apparatus 622 is configured to remain in the straight position, and can be utilized with a straight electrode array, as depicted in the above figures. Additional details of this are described below.

As noted above, the conductive apparatus 622 is configured such that an impedance between any two locations on the interior surface of the passage 624 within a distance corresponding to the distance between two electrodes 148 of the electrode array 146 that will be inserted or otherwise located within passage 624 is less than about 500 ohms. In an exemplary embodiment, the aforementioned impedance is less than about 1500, 1400, 1300, 1200, 1100, 1000, 900, 800, 700, 600, 500, 400, 300, 200, 100, 50 or 25 ohms or less or any value or range of values therebetween in about 1 ohm increments (444 ohms to about 32 ohms, 458 ohms, 55 ohms, etc., where "about" also corresponds to a disclosure of the exact amount as used herein). It is noted that in some embodiments, the aforementioned impedance is based on the impedance of other components of the system (e.g., the impedance of the leads of the electrode array). In at least some exemplary embodiments, at least some of the aforementioned impedances have utilitarian value with respect to enabling the teachings detailed herein and/or variations thereof with respect to testing for an open circuit between two electrodes. It is noted that for embodiments where the conductor is moved in and out pf position, the impedance of the conductor can be of various values that have utility, and thus some embodiments will have impedance values that are different than others, and many embodiments will have overlapping impedance values with other embodiments.

It is noted that in at least some exemplary embodiments, the apparatus 400 is configured such that the conductive apparatus 622 can be removed or otherwise moved away from the electrode array 146 while the electrode array 146 remains sealed in a sterile manner within the package 410 so that the conductivity achieved between two electrodes enabling the testing for the open circuit is no longer present, thus enabling testing for a short circuit between two or more of the electrodes. In an exemplary embodiment, the apparatus 400 is configured to enable the conductive apparatus 622 to be pulled away from the electrode array 146. In some exemplary embodiments, conductive apparatus 622 is configured to separate in half so that it can be manipulated away from the electrode array 146 via manipulation through the package 410. Some additional features of this concept will be described below in greater detail, but it is noted at this time that, in an exemplary embodiment, the apparatus 400 is thus configured to disable the enablement of the testing for the open circuit while the electrode assembly 146 is sterilely sealed in the package so as to enable testing for a short circuit.

Conversely, in at least some exemplary embodiments, the conductive apparatus 622 is configured so as to enable both testing for an open circuit and testing for a short circuit without moving the conductive apparatus 622 relative to the electrode array 146. By way of example only and not by way of limitation, the conductive apparatus 622 is configured to have a "midrange" impedance between two locations on the inner surface of passage 624 corresponding to the location of where two electrodes 148 of the electrode array 146 is located in the passage 624 contact the inner surface of passage 624. By way of example only and not by way of limitation, in an exemplary embodiment, the impedance between the two locations could be about 4,000 ohms. In an exemplary embodiment, such can have utilitarian value with respect to a cochlear implant 100 where an open circuit is defined as impedance greater than 30,000 ohms, and a short circuit is defined as impedance less than 500 ohms. In this regard, by way of example, utilizing ohms law with a given voltage and a given current, because the impedance between two electrodes is known (at least with an accuracy to enable utilitarian execution of the teachings detailed herein), and because the impedance of the remainder of the system is also known, (at least with an accuracy to enable the utilitarian execution of the teachings detailed herein), simultaneous testing for an opened and short circuit can be executed. By way of example only and not by way of limitation, for a given applied current at a given applied voltage at a given lead by current generator/detector 1040, the detected current and/or voltage at one or more other leads should fall within a predetermined range. In an exemplary scenario, if the current and/or voltage at one or more other leads falls below a predetermined range (e.g., a range that is based on a conductive path established by conductive apparatus 622 that has an impedance of 4000 ohms between electrodes 1 and electrode 2 (i.e., hypothetical lead 1010 establishes a conductive path having such an impedance)) it can be deduced that there exists an open circuit. Conversely, in an exemplary scenario, if the current and/or voltage at one or more other leads falls above a predetermined range, it can be deduced that there exists a short circuit. In either or both scenarios, the determination can be made that the cochlear implant 100, or at least the associated electrode array assembly 190, should not be or otherwise is not in condition for implantation to a recipient at the current time, and another cochlear implant 100, or at least another electrode array assembly 190, can be obtained.

Thus, in an exemplary embodiment, the apparatus 400 is configured to provide conductivity between two electrodes of the electrode assembly sufficient to enable testing for an open circuit between the two electrodes while also enabling testing for a short circuit between the two electrodes with the conductivity present between the two electrodes.

It is noted that the above impedance of 4000 ohms of the conductive apparatus 622 is but an exemplary impedance. Any impedance between two locations of the passage 624 that contact two or more electrodes of an electrode array 146 that can enable the teachings detailed herein and/or variations thereof to be practiced can be utilized in at least some exemplary embodiments. In this regard, in an exemplary embodiment, the impedance can be about 1000, 1500, 2000, 2500, 3000, 3500, 4000, 4500, 5000, 5500, 6000, 6500, 7000, 7500, 8000, 8500, 9000, 9500, or 10000 or more ohms or any value or range of values therebetween in 1 ohm increments.

Thus, in an exemplary embodiment, the apparatus includes a portion made of a material that directly contacts the two electrodes to establish the conductivity therebetween having an impedance of about 200 ohms to about 4.7 megaohms.

While the embodiments detailed above have been directed towards the utilization of a conductive apparatus 622 that is separate from the package 410, in some alternate embodiments, the conductive apparatus 622 can be integral with the package 410. Indeed, in an exemplary embodiment, the conductive apparatus is the package 410 (at least an interior portion thereof). By way of example only and not by way limitation, in at least some exemplary embodiments, at least a portion of the package 410 is made of a conductive material in direct contact with electrodes of the electrode assembly, which can subsequently be moved away from the electrodes to enable testing for a short circuit. In an exemplary embodiment, the package 410 can be manipulated to be in contact with the electrodes so as to enable testing for an open circuit, and then be manipulated to no longer be in contact with electrodes so as to enable testing for a short circuit.

Concomitant with the enablement of testing for an open circuit, it is further noted that in an exemplary embodiment, the apparatus 400 can be configured to vary the impedance between two or more electrodes so as to first conduct a test for an open circuit, and then subsequently conduct a test for a short circuit, or vice versa. Additional details of this will be described in greater detail below. First, however, some exemplary methods will now be described.

Figure 12:
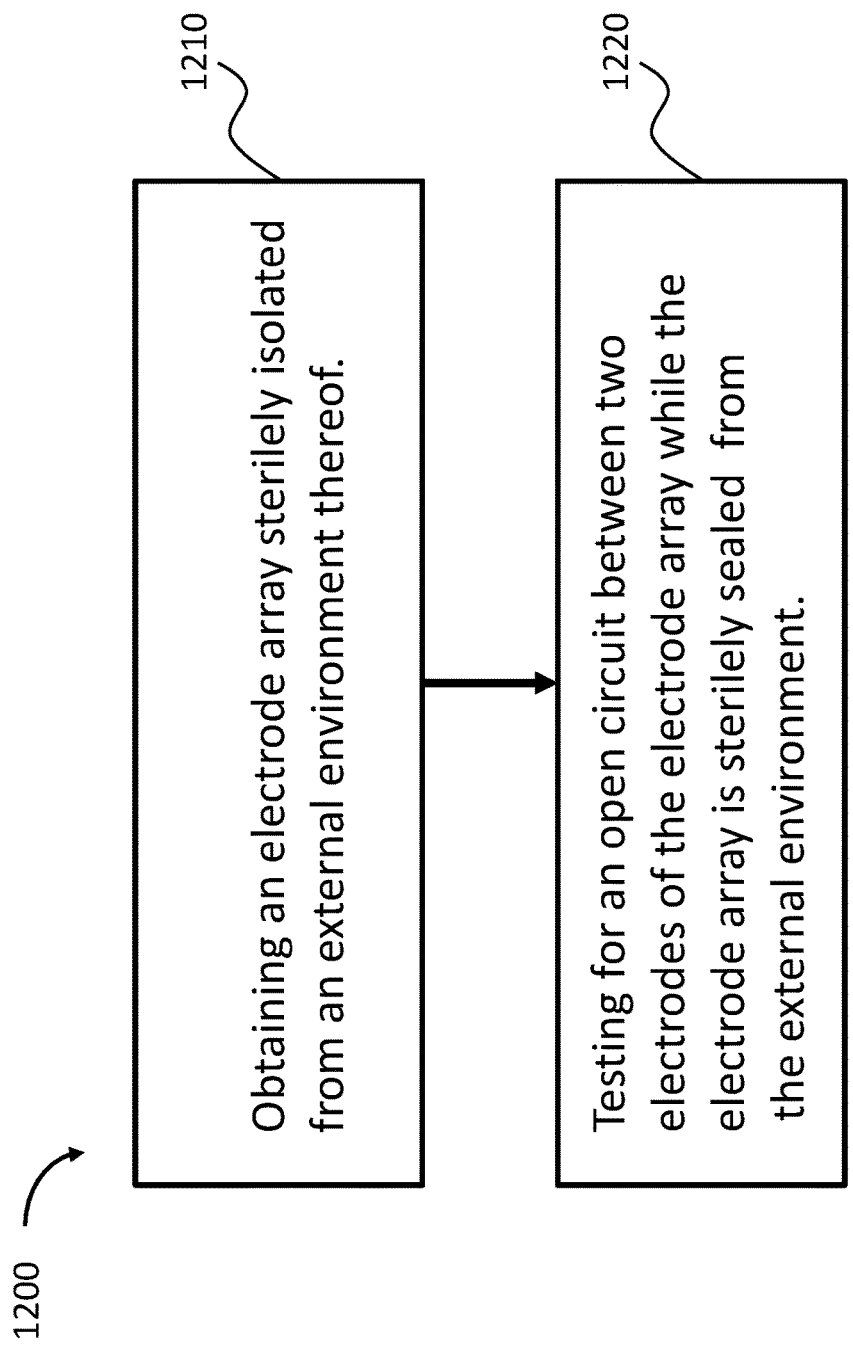
FIG. 12 presents a flow chart for an exemplary method according to an exemplary embodiment.

Referring now to FIG. 12, there is presented an exemplary flow chart 1200 representing an exemplary algorithm for an exemplary method. Method 1200 includes method action 1210, which entails obtaining an electrode array, such as by way of example, electrode array 146 of electrode array assembly 190, which is sterilely isolated from an external environment thereof. In an exemplary embodiment, method action 1210 can be executed by obtaining the apparatus 400, which, as detailed above, includes the package 410, and the cochlear implant 100 sterilely sealed therein. Method action 1200 also includes method action 1220, which entails testing for an open circuit between two electrodes of the electrode array while the electrode array is sterilely sealed from the external environment. In an exemplary embodiment, method action 1220 can be executed by utilizing the conductive apparatus 622 that is located in package 410 is detailed above. Alternatively, in an alternate exemplary embodiment, method action 1220 can be executed utilizing a conductive package 410, where the package material is in contact with the electrodes of the electrode array such that a sufficiently conductive path exists between the electrodes. Method action 1220 can be executed utilizing other devices systems and/or methods as detailed herein and/or variations thereof.

Figure 13:
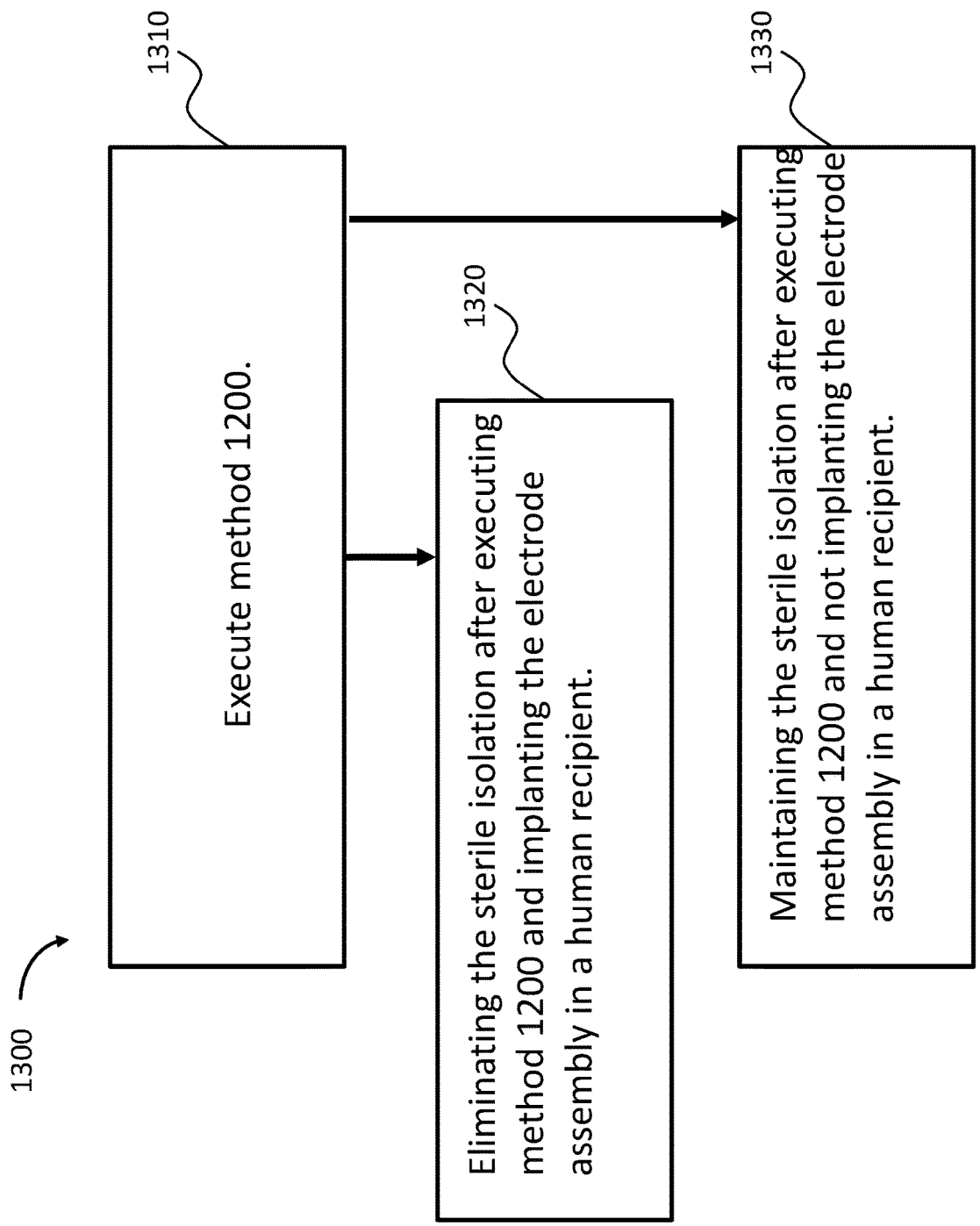
FIG. 13 presents a flow chart for an exemplary method according to an exemplary embodiment.

As detailed above, in an exemplary embodiment, there is utilitarian value with respect to the ability to test for an open circuit in the cochlear implant 100, or at least in the electrode array assembly 190 thereof, while the pertinent components are sterilely sealed within the package 410, in relatively close temporal proximity to implantation of the pertinent components in a recipient. FIG. 13A presents an exemplary flow chart 1300A, representing an exemplary method that includes method action 1310, which entails executing method 1200. Method 1300 further includes method action 1320, which entails eliminating the sterile isolation of the obtained electrode array after executing method 1200 (e.g., after testing for an open circuit) and implanting the electrode assembly in a human recipient. In an exemplary embodiment, method action 1320 is executed only after a determination is made that the tests for an open circuit result in the presence of no open circuit. That is, if the action of testing for an open circuit between two electrodes results in an indication that there exists an open circuit, in at least some exemplary embodiments, method action 1320 is not executed. Instead, method action 1330 executed, which entails maintaining the sterile isolation after executing method 1200 and not implanting the electrode assembly in a human recipient. In an exemplary embodiment, method 1300 can have utilitarian value in that the package 410 is always maintained. In an exemplary embodiment, the apparatus 400 can be returned to the supplier, at least upon a determination that an open circuit is present (as well as a short circuit, in some alternate embodiments) such that the cochlear implant 100 is maintained in its original package without that package being opened.

As detailed above, in an exemplary embodiment, there is utilitarian value with respect to conducting method 1200 in close temporal proximity to the implantation procedure. In an exemplary embodiment, the action of testing for an open circuit (method action 1220) includes testing for the open circuit while the recipient of the electrode array is under anesthesia and prepared for implantation. In this regard, in an exemplary embodiment, the recipient can be in the operation room/implantation room, anesthetized for the surgery/implantation process, while method action 1220 is executed. Method action 1220 can be executed in the operating room, or can be executed in a location that enables the implantation process to be executed in a manner that meets medical regulations and/or laws in a given jurisdiction in which the method is executed. Note that the recipient need not necessarily have been "opened" for surgery. That is, the meaning of prepared for implantation does not require that the recipient be "opened" at the time method action 1220 is executed. By way of example only and not by way of limitation, method action 1220 can be executed, and then, upon a determination that the cochlear implant 100, or at least the electrode array assembly 190, is in a sufficient condition for implantation, the utilitarian incisions in the recipient can be made thereafter.

Corollary to the above is that in an exemplary embodiment, the apparatus 400 is configured such that the electrode array in a state prepared for immediate implantation into a human recipient upon opening of the package. By "immediate implantation," it is meant that the electrode array 146, and, in some instances, the cochlear implant 100 can be removed from the package 410 and directly placed in the recipient from the package 410, although there might be ancillary actions taken in between the opening of the package 410 in the implantation.

In an exemplary embodiment, the teachings detailed herein can have utilitarian value in that testing for an opened and/or a short circuit can be conducted within the sterile packaging 410. It is noted that the testing can be performed during manufacturing, before the device leaves the assembly location but after packaging and/or after sterilization. Accordingly, in an exemplary embodiment, there is a method that includes manufacturing the cochlear implant 100, or at least obtaining the cochlear implant 100, and placing the cochlear implant 100, or at least the electrode array assembly 190, in the package 410. The method further entails the action of sterilizing the interior of the package 410 with the cochlear implant 100, or at least the electrode array assembly 190 located therein, and thus sterilizing the outer surfaces of those components located therein. In an exemplary embodiment, in relatively close temporal proximity, or at least prior to shipping of the resulting apparatus 400 from the facility where the sterilization action is taken place, method 1200 is executed. During the execution of method 1200, testing for a short circuit can also be executed. Upon a determination that there are no open circuits and/or no close circuits and/or that the cochlear implant 100 with the pertinent components thereof are in condition for implantation, the apparatus 400 is shipped from the facility where the sterilization has taken place. As detailed above, method 1200 can be again executed at the location where the cochlear implant 100, or at least the electrode array assembly 190, is to be implanted in the recipient. In the event that a determination is made that there exists a failure mode within the cochlear implant 100, or at least the pertinent portion of the electrode array assembly 190, the apparatus 400 is returned to the manufacturer or otherwise to the entity that placed the apparatus 400 into the stream of commerce. This returning action is executed with the sterile packaging intact. This enables the cochlear implant 100, or at least the electrode array assembly 190, to be retested in a controlled environment (e.g., method action 1200 can be re-executed, alone and/or along with a test for a short circuit), and these components can be salvaged if no fault is actually present. In an exemplary embodiment, this can simply entail again placing the apparatus 400 back into the stream of commerce (e.g., shipping the apparatus 400 to an implantation site, where the packaging 410 was never opened, because the pertinent testing was performed utilizing the communication system detailed herein). In an alternate exemplary embodiment, this can entail repackaging the cochlear implant 100, or other pertinent portion thereof, and re-sterilizing the interior of the new package 410 (or the old packaging if such is reused), and executing one or more or all of the methods detailed herein and then shipping the apparatus 400 to the implantation site.

Note further that the testing for an open circuit can be executed before the patient is anesthetized and prepared for surgery. Note further, that the testing for an open circuit can be executed before the patient is anesthetized and prepared for surgery, and subsequently while the patient is anesthetized and prepared for surgery.

In view of the above, method 1300 includes the action of determining whether to implant the electrode array in the recipient based on the testing (method action 1220). With respect to the flow chart of FIG. 1300, the action of determining whether to implant electrode array in the recipient based on the testing is executed between boxes 1310 and 1320 under one set of circumstances, and between boxes 1310 and 1330 under the opposite set of circumstances.

Figure 14:
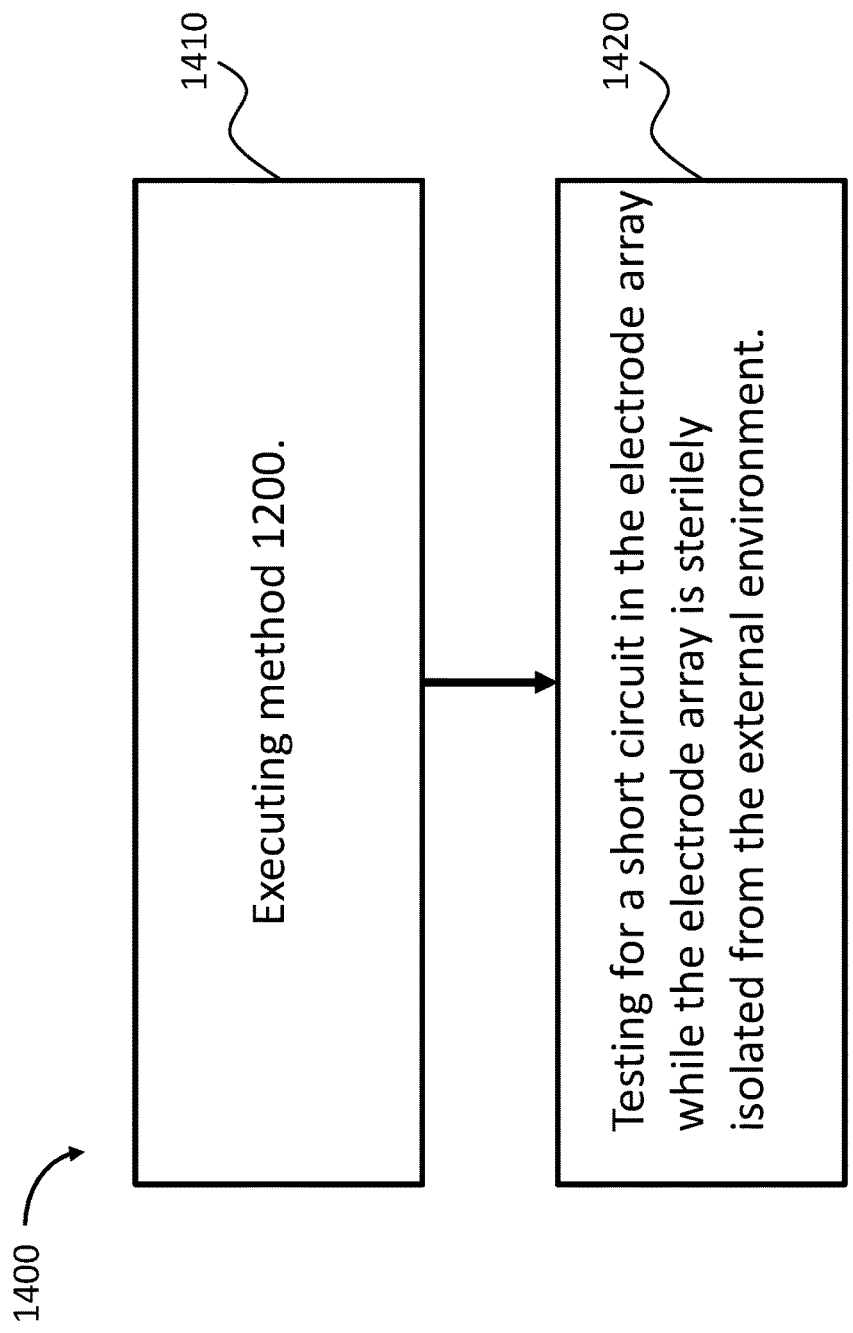
FIG. 14 presents a flow chart for an exemplary method according to an exemplary embodiment.

As detailed above, the testing for the open circuit can be executed along with testing for a short circuit. Accordingly, FIG. 14 presents flowchart 1400, which entails first executing method 1200, and then executing method 1420, which entails testing for a short circuit in the electrode array while the electrode array is sterilely isolated from the external environment. In an exemplary embodiment, method action 1420 is executed while the cochlear implant 100, or at least the electrode array assembly 190, is located in a sterile manner in the package 410 (i.e., before the package 410 is unsealed/opened). While the embodiment of FIG. 14 is presented in terms of first executing method action 1200, and thus executing testing for an open circuit, prior to executing method 1420, in an alternative embodiment, method action 1420 is executed prior to the execution of method action 1220. That is, the testing for the short circuit can be executed prior to the testing for the open circuit. Note further that in some embodiments, testing for one or more open circuit can be executed followed by testing for one or more short circuits, followed by testing for one or more other open circuits followed by testing for one or more short circuits etc., or vice versa. Any order in which the method actions detailed herein that can be practiced to enable the utilitarian teachings detailed herein and/or variations thereof can be practiced in at least some exemplary embodiments.

As noted above, exemplary embodiments of apparatus 400 can enable the application of different conductive paths having different impedances (which includes the elimination of a conductive path entirely, or at least substantially entirely) between given electrodes, so that testing for an open circuit and testing for a short circuit can be executed while the electrode array assembly 190 remains sterilely sealed within the package 410. Additional features of this will be described below. However, briefly, it is noted that in some embodiments, this entails removing or otherwise eliminating contact between electrodes of the electrode array 146 and the passage 624 of the conductive apparatus 622. In some embodiments, this entails changing the impedance of a given conductive path. Again, as will be detailed below, there are other implementations that can enable the aforementioned different impedances to be obtained. In any event, in an exemplary embodiment, any of the methods detailed herein, such as by way of example, method 1400, can be executed by executing the additional method action of manipulating a package apparatus forming the sterile isolation of the cochlear implant 100 from the external environment from a first state to a second state and subsequently testing for one of an open circuit or a short circuit of the electrode assembly while the electrode array is sterilely isolated from the ambient environment. In an exemplary embodiment, the package apparatus includes the package 410, and the conductive apparatus 622. That said, as mentioned above them will be further detailed below, in an exemplary embodiment, method 1400 can be executed by practicing the additional method action of manipulating package material forming the sterile isolation of the cochlear implant 100 from the external environment from a first state to a second state and subsequently testing one of an open circuit or a short circuit of the electrode assembly while the electrode array is sterilely isolated from the ambient environment. That is, as noted above (and as will be detailed further below) the conductive path that enables testing for an open circuit can be established by utilizing the package material of package 410.

Note further, in an exemplary embodiment, there is an exemplary method that entails testing for the other of the open circuit or the short circuit while the package material is in the first state.

Also, concomitant with the teachings detailed above, in an exemplary embodiment, any of the testing detailed herein, such as by way of example only and not by way of limitation, the testing for the open circuit and/or a short circuit, is executed using inductive communication to activate a stimulator to provide an electrical signal to the electrode array. In this regard, in an exemplary embodiment, the black box current generator/detector 1040 corresponds to the receiver/stimulator 180 of the cochlear implant 100.

Additional details of the inductive communication features, and the communication features in general, are described below.

Some specific examples of implementations of some exemplary embodiments will now be described.

Figure 15:
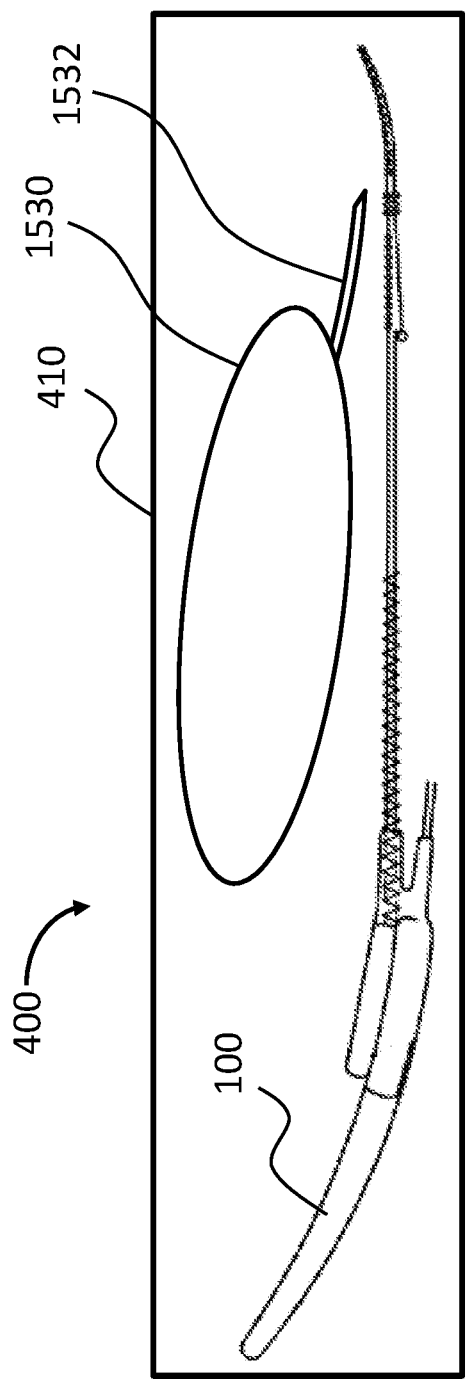
FIG. 15 is a schematic of another example of an apparatus according to an exemplary embodiment.

As noted above, in an exemplary embodiment, the impedance between electrodes can be varied while the electrodes are sterilely sealed in the package 410. In an exemplary embodiment, a fluidic apparatus is utilized to controllably place the electrodes 148 of the electrode array 146 into contact with the fluid so as to establish a conductive path between the electrodes, which path is not present prior to the contact of the electrodes of the fluid. In this regard, by way of example only and not by way of limitation, FIG. 15 depicts an exemplary apparatus 100 that includes a blister pack 1530 filled with a conductive fluid or otherwise low impedance fluid, such as by way of example only and not by way of limitation, saline. During normal shipping and storage of the apparatus 400, blister pack 1530 is fluidically isolated from the other portions of the interior of the package 410, even though, in at least some embodiments, the blister pack 1530 is located in the package 410. In an exemplary embodiment, the testing for the short circuits can be executed with the fluid located in blister pack 1530 sealed therein. That is, the testing for the short circuit can be conducted utilizing the relatively high impedance between given electrodes. In this regard, in an exemplary embodiment of this implementation, the material of the package 410 is a relatively high impedance material such that even if the material of the package 410 contacts the electrodes of the electrode array 146, the package 410 will not provide a low impedance path between the electrodes, thus permitting the testing for the short circuits to be executed. Note further that in an exemplary embodiment, the electrode array 146 is located in a sheath or a cap that is made of a high impedance material, thus electrically isolating the electrodes 148 from the body of the packaging material.

After testing for the short circuits, the blister pack 1530 can be ruptured so as to eject the fluid located therein into the remainder of the package 410 (still while maintaining the internal environment of the package 410 in a sterile condition). In an exemplary embodiment, the blister pack 1530 can be provided with a spout 1532 that directs the fluid towards the electrodes of the electrode array 146. In an exemplary embodiment, the package 410 can be held in an orientation such that the fluid from blister pack 1530 pools at portion of the package where the electrode array 146 is located (e.g., with respect to the view of FIG. 15, the apparatus 400 would be rotated approximately 90°). In an exemplary embodiment, the package 410 is configured such that the quantity of fluid located in the blister 1530, after it is ejected therefrom, sufficiently fills the "bottom" of the package 410 so as to ensure that the low impedance fluid is in contact with the pertinent electrodes. Upon such fluid conductive the being present, testing for the open circuits is executed.

Figure 16:
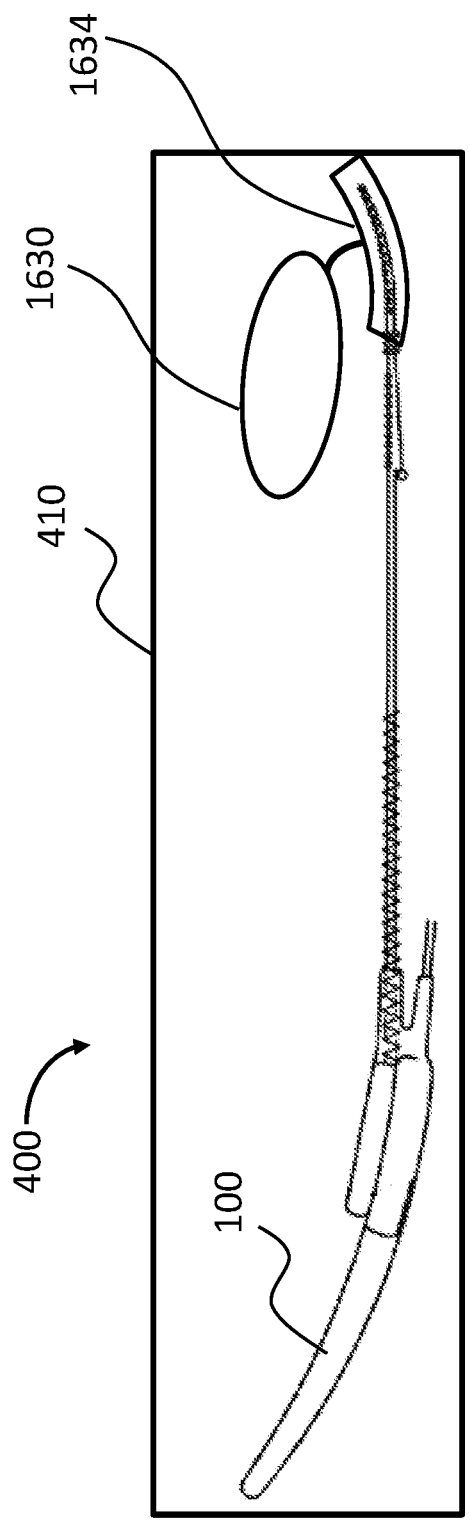
FIG. 16 is a schematic of another example of an apparatus according to an exemplary embodiment.

It is noted that in some exemplary embodiments, the fluid located in blister pack 1530 can be corralled such that it is less likely to contact other portions of the cochlear implant 100, regardless of the orientation of the package 410. FIG. 16 presents such an exemplary embodiment, where blister pack 1630 is in fluid communication with pocket 1634 which surrounds the entire electrode array 146 in a manner that prevents or otherwise effectively limits the amount of fluid that can escape from pocket 1634 when the fluid from pack 1630 is ejected into pocket 1634. In an exemplary embodiment, element 1634 is a sheath or a cap. In some embodiments, the sheath/cap 1634 is configured to seal the fluid therein (i.e., at least substantially prevent the fluid from escaping out of element 1634 into the remainder of the package.

Figure 17:
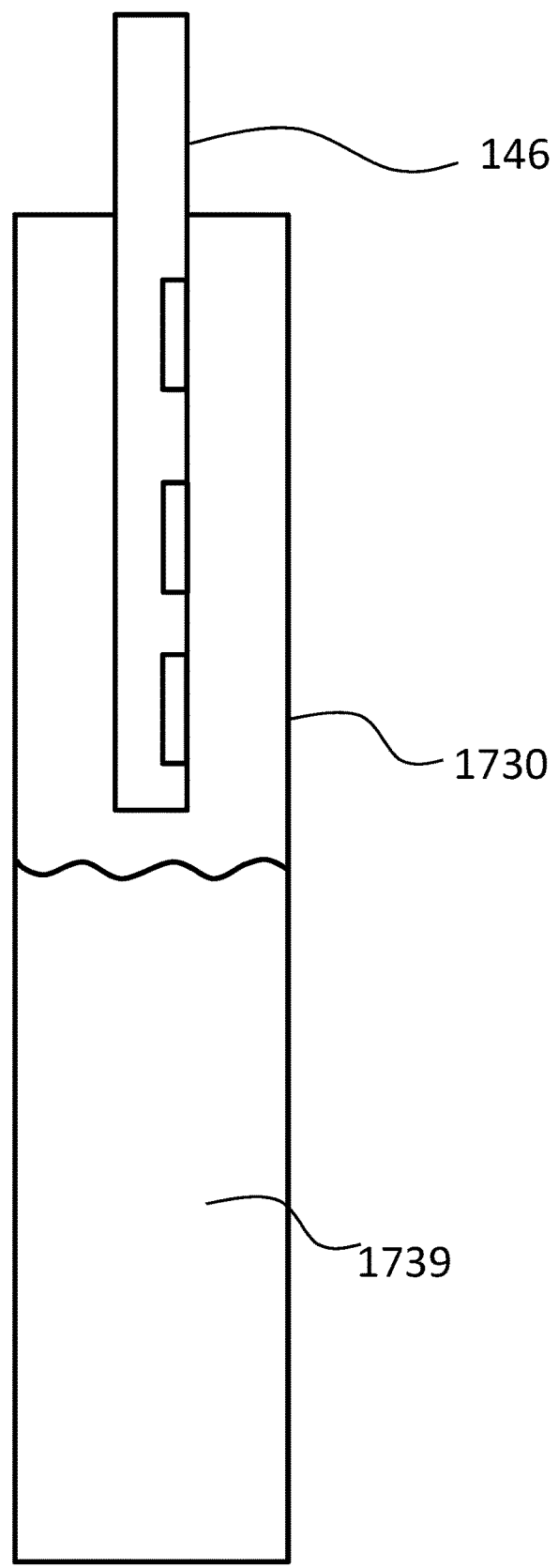
FIG. 17 is a schematic of a component of an exemplary apparatus according to an exemplary embodiment.

Still further, it is noted that in at least some exemplary embodiments, the fluid utilized to establish the low impedance connections between the electrodes is not necessarily isolated from the electrodes during testing for the short circuits. In this regard, with respect to FIG. 17, an exemplary arrangement depicts container 1730, which forms a generally sealing arrangement about electrode array 146 such that the electrodes thereof or located within the container 1730. The container is approximately half filled with the fluid of low impedance 1739, although different relative volumes of fluid can be utilized providing that the teachings herein can be enabled. In an exemplary embodiment, the apparatus 400 is positioned such that gravity draws the fluid 1739 away from the electrodes of the electrode array 146, which configuration is depicted in FIG. 17. In such a configuration, testing for a short circuit can be executed, at least after a sufficient amount of time has elapsed such that gravity draws away residual fluid that might remain on the array 146 that could interfere with the testing for the open circuit. In an exemplary embodiment, the apparatus 400 is then flipped upside down such that the fluid flows towards the array 146 and surrounds all of the electrodes. In such a configuration, testing for the open circuits can be executed. It is noted that in some exemplary embodiments, the testing for the open circuits can be executed before the testing for the short circuits. That said, in an alternate embodiment, a frangible or otherwise breakable barrier can be located between the array 146 and the fluid 1739 with in the container 1730 (e.g., analogous to or the same as the principle of operation associated with the aforementioned blister packs). That is, in an exemplary embodiment, the electrodes can normally be stored or otherwise maintained in an air environment, or whatever environment is utilized within the package 410, and then the electrodes can be immersed in the low impedance fluid to execute testing for an open circuit. Any device, system, and/or method that can enable the utilization of fluid to implement the teachings detailed herein and/or variations thereof can utilize in at least some exemplary embodiments.

Figure 18:
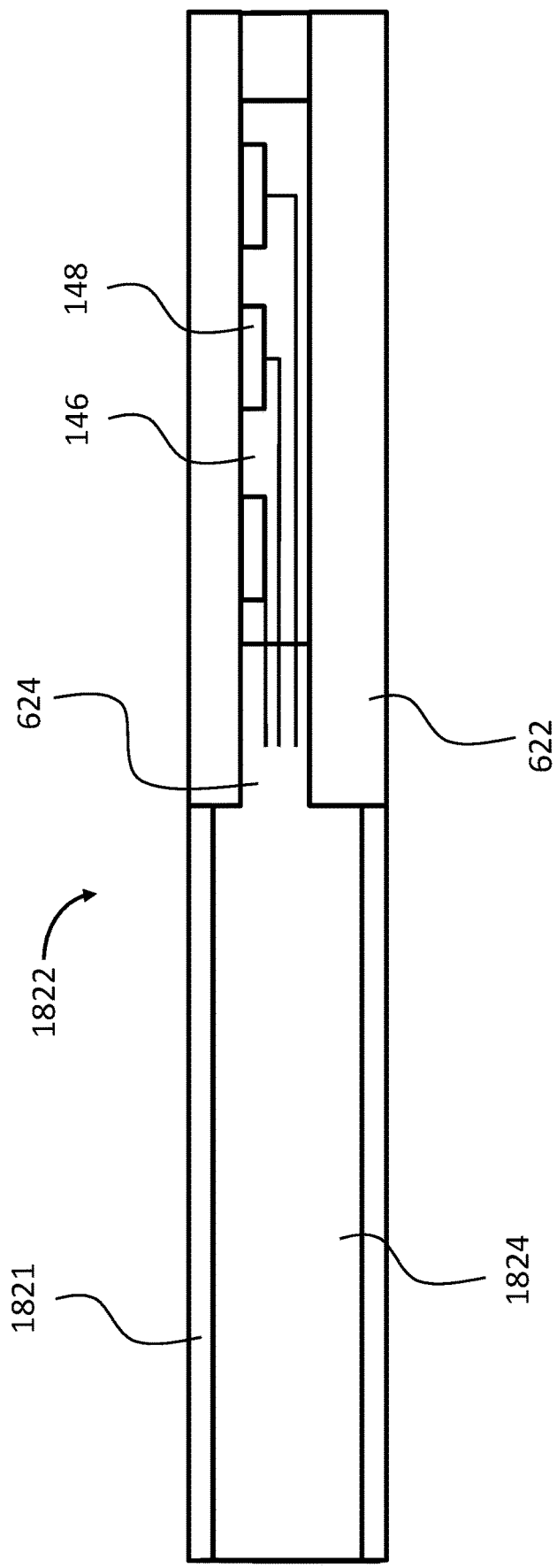
FIGS. 18-20 are schematics of a component of an exemplary apparatus according to an exemplary embodiment.

FIG. 18 depicts an alternate embodiment of an apparatus configured to vary the impedance between electrodes so as to enable testing for both open circuits and close circuits. In the exemplary embodiment depicted in FIG. 18, conductive apparatus 1822 includes a portion 622 corresponding to the conductive apparatus 622 detailed above, and another portion 1821 made from a nonconductive material/material having a relatively high impedance. That said, in an alternate embodiment, the material of the portion 1821 can be made of a material having a relatively low impedance, such as the material of conductive apparatus 622, but portion 1821 is configured such that the interior thereof represented by reference numeral 1824 is sufficiently spaced apart from the electrodes 148 a sufficient distance such that testing for a short circuit between the electrodes can be conducted when the array 146 is located therein. That is, if there is sufficient space 1824 between the interior surface of 1821, even if the portion 1821 is made of a conductive material, testing for a short circuit can be executed providing that the electrodes 148 are not in contact with the surface of portion 1821.

Figure 19:
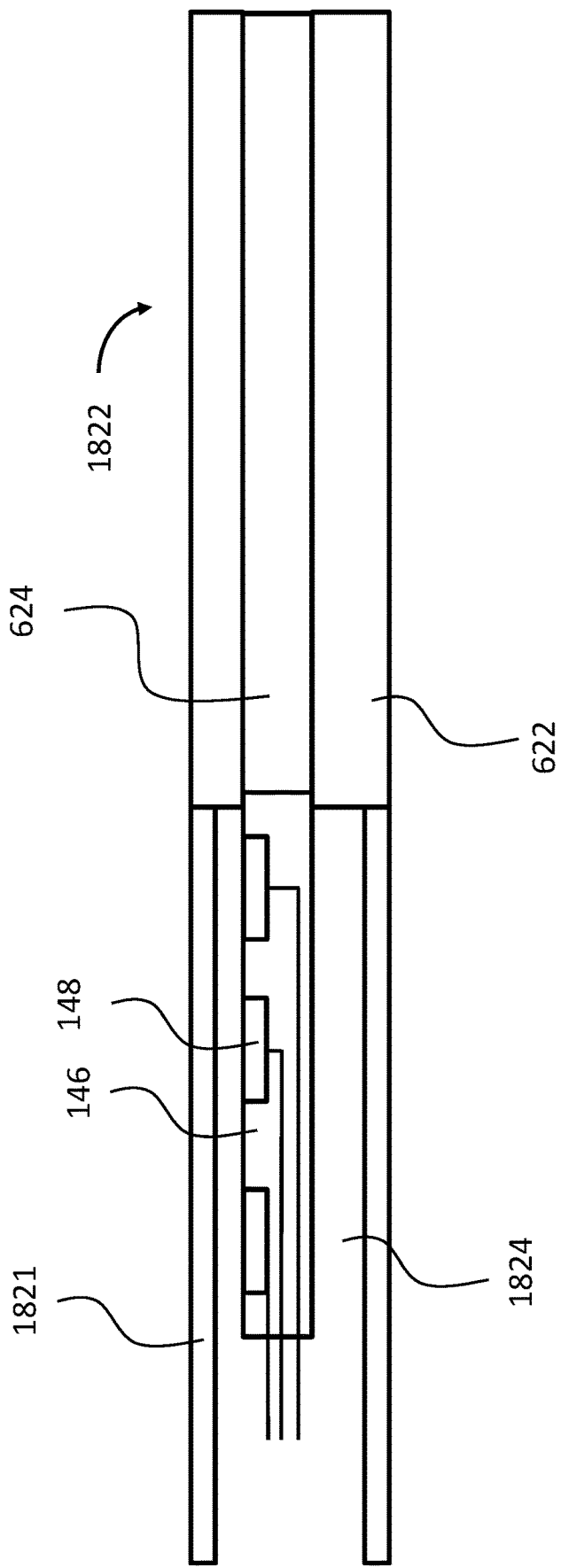

Accordingly, with respect to FIG. 18, when the electrode array 146 is located in portion 622, open testing can be executed according to the teachings detailed herein. In an exemplary method, after the open testing is executed, the apparatus 1822 is moved relative to the electrode array 146 such that the electrode array 146 is no longer inside the interior 624 of the conductive apparatus 622, or, more relevantly, such that the interior surface of conductive apparatus 622 is no longer in contact with the electrodes of the electrode array 146, as can be seen in FIG. 19. Note that in some embodiments, apparatus 1822 is moved relative to the electrode array 146, while in other embodiments, it is the electrode array 146 that is moved relative to the apparatus 1822. Still further, both can be moved relative to one another. Accordingly, in an exemplary embodiment, the apparatus 400 is configured to enable movement of the electrode array 146 relative to the apparatus 1822 and/or enable movement of the apparatus 1822 relative to the array 146.

In the configuration as presented in FIG. 19, testing for the short circuit can be executed.

It is further noted that an exemplary method action can entail moving conductive apparatus 622 away from the electrode array 146, where there is no portion 1821 that is part of the conductive apparatus. That is, in at least some exemplary embodiments, portion 1821 is not necessary to practice testing for close circuits, at least not embodiments where the material of the package 410 is of a relatively high impedance material such that even if there is contact between the package 410 in the electrodes 148, testing for the close circuits can still be executed.

Figure 20:
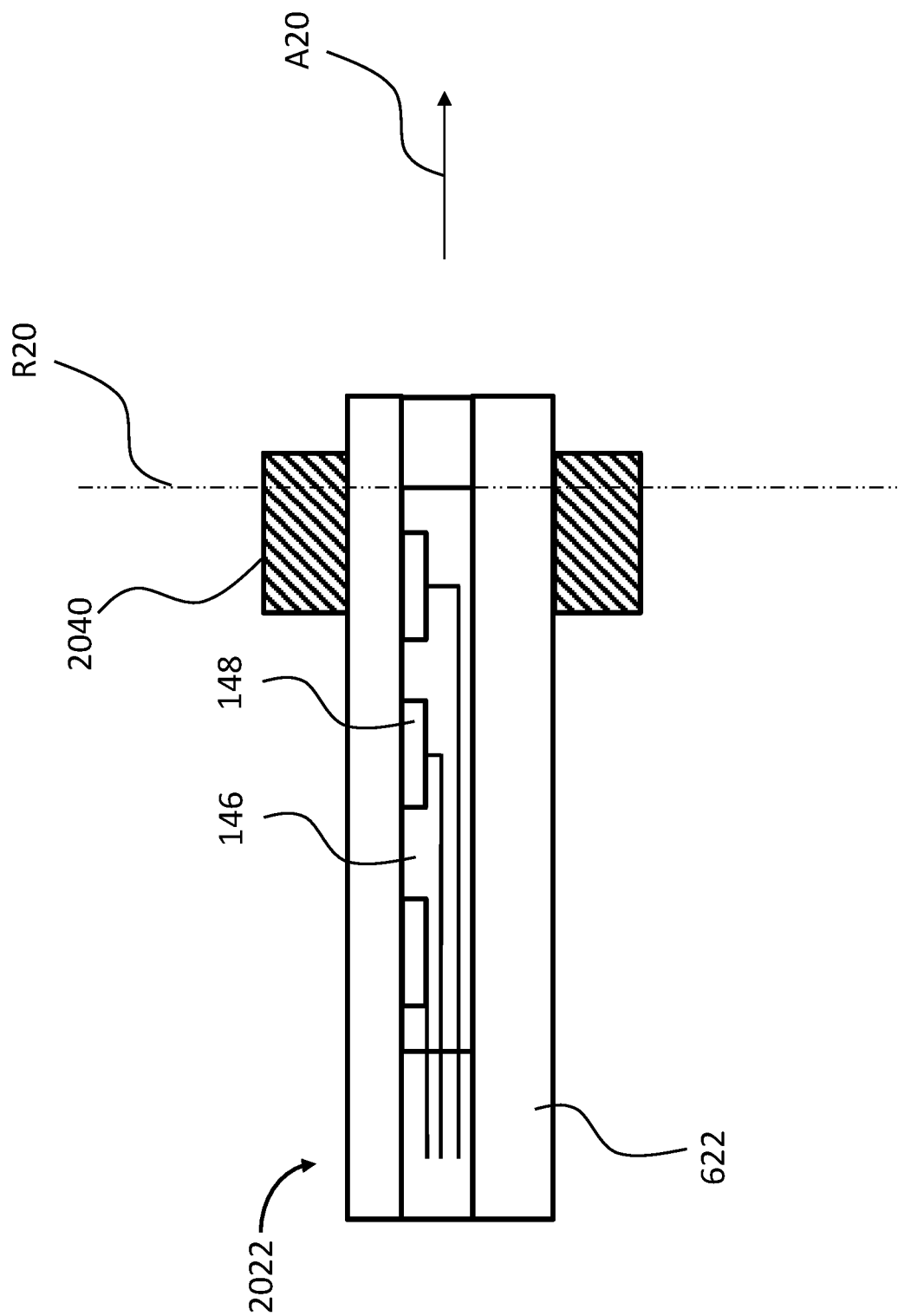

Any arrangement that can enable the movement of the electrode array 146 and/or the conductive apparatus 622 (which includes apparatus 1822) can be utilized in at least some exemplary embodiments. In an exemplary embodiment, magnetic forces can be utilized to move the conductive apparatus relative to the array 146 and/or vice versa. In this regard, FIG. 20 depicts an exemplary conductive apparatus 2022, which corresponds to conductive apparatus 622 detailed above, with the addition of a magnet 2040 located on the outer surface of the conductive apparatus 622 (any arrangement of magnet located anywhere that can enable the teachings detailed herein and/or variations thereof can be utilized in at least some exemplary embodiments). For purposes of illustration, reference line R20 is superimposed on the tip of the electrode array 146 in FIG. 20, and relative movement is with reference to R20. In an exemplary embodiment, all of the components depicted in FIG. 20 are located within the package 410 in a manner such that those components are sterilely sealed therein (e.g., along with the other components of the cochlear implant 100).

According to an exemplary method, testing for an open circuit is executed with the array 146 located within the conductive apparatus 2022 as depicted in FIG. 20.

Figure 21:
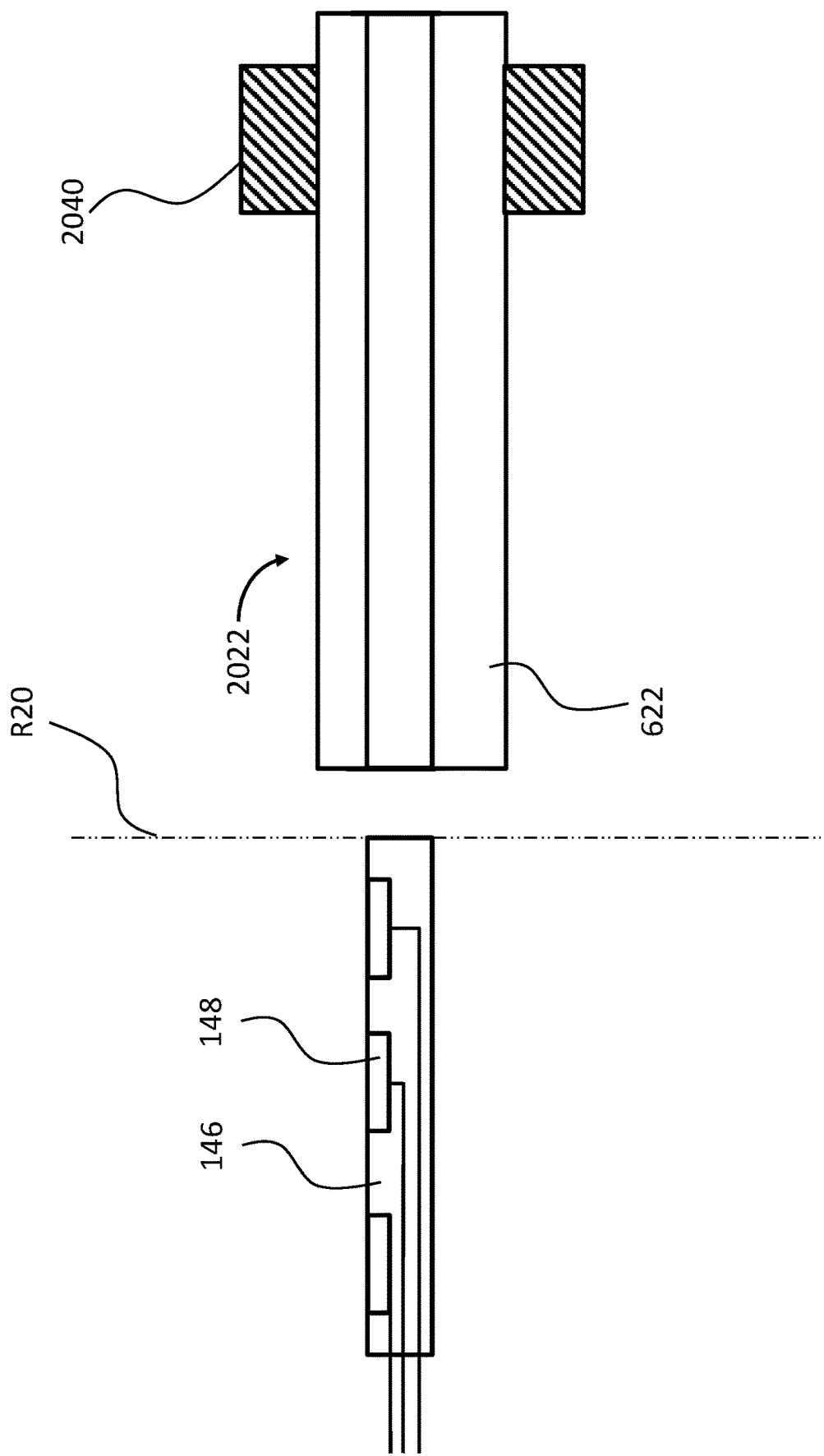
FIG. 21 is a schematic of a component of an exemplary apparatus according to an exemplary embodiment in use.

In an exemplary embodiment, after the testing for the open circuit is executed, a magnet located outside the package 146 is placed into the magnetic field associated with magnet 2040, and via the magnetic attraction and/or repulsion that results from the two different magnets, the conductive apparatus 2022 is pushed and/or pulled relative to the electrode array 146 in the direction of arrow A20. In this exemplary method, the apparatus 400 is configured so as to hold the electrode array assembly 190 in a relatively stationary location relative to the package 410 while the conductive apparatus 2022 is moved in the direction of arrow A20. The conductive apparatus 2022 is pushed and/or pulled utilizing the magnet located on the outside of the package 410 via magnetic interaction with the magnet 2040, which is located on the inside of the package 410, until the conductive apparatus 2022 is located away from the array 146 or otherwise such that the electrodes 148 are no longer in contact with the inner surface of the conductive apparatus 622 or at least such that there is no longer a low impedance conductive passageway between the electrodes 148 (at least not one resulting from the conductive apparatus 622). When the conductive apparatus 2022 is located as seen in FIG. 21, for example, or otherwise located such that testing for a short circuit can be executed, the testing for the short circuit is executed. According to this exemplary embodiment, the conductive apparatus 2022 can be moved relative to the electrode array 146 so as to enable testing for both open circuits and close circuits, without opening the package 410 or otherwise disturbing the sterility of the interior of the package 410. Accordingly, in an exemplary embodiment, the conductive apparatus 622 can be moved remotely.

Note further that there are other exemplary manners in which the conductive apparatus 622 can be moved relative to the electrode array 146 and/or vice versa. In an exemplary embodiment, the conductive apparatus 622 can simply being manipulated through the package material 410 by hand. In an exemplary embodiment, the conductive apparatus 622 can be in the form of conductive apparatus 2022, and thus can have a magnet, but the magnet is not necessarily needed if the conductive apparatus 2022 can be manipulated by hand so as to be moved from the position to enable testing for the open circuit to the position to enable testing for a short circuit. In this regard, the magnet 2040 can be utilized as a backup in the event that hand manipulation cannot be accomplished.

Gravity manipulation can also be utilized. G-force manipulation can be utilized as well (e.g., expose the package to a sufficiently high acceleration or deceleration to move the conductive apparatus relative to the electrode array.

Figure 22A:
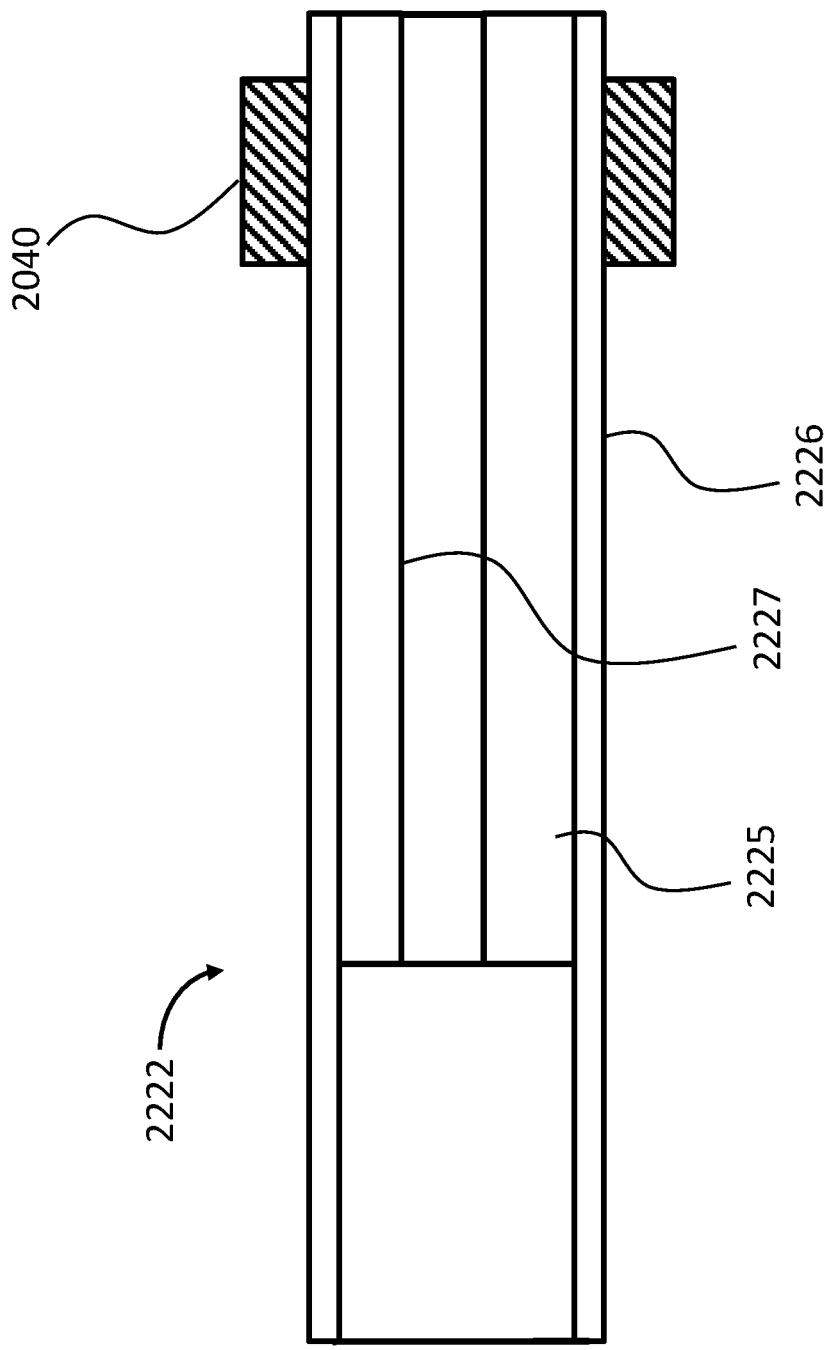
FIGS. 22A-25B are schematics of various components exemplary apparatuses according to exemplary embodiments.

It is briefly noted that the conductive apparatus 622 can be a tube filled with conductive foam or the like, as seen in FIG. 22A. In this regard, by way of example only and not by way limitation, there is an exemplary conductive apparatus 2222, that includes a tube 2226 in which is located or otherwise supports foam 2225. In an exemplary embodiment, the tube 2226 can be plastic or some other type of material, and the foam can be a foam that is embedded with a conductor such as by way of example only and not by way of limitation, carbon or the like, or any other material that can enable the impedance is to be achieved so as to practice the teachings detailed herein and/or variations thereof. In an exemplary embodiment, conductive apparatus 2222 can be considered an electrode sleeve.

While the above embodiments have been described in terms of first executing testing for the open circuit, and then moving the conductive apparatus away from the electrode array 146 (and/or visa-versa) to perform testing for the close circuit, in an alternate embodiment, testing for the short circuit can be first executed, and then the conductive apparatus can be moved to be located against the electrode array 146 to establish the requisite conductive paths, after which testing for the open circuit can be executed.

It is noted that in an exemplary embodiment, the foam is a relatively high impedance material, but the apparatus 400 is configured to expose the foam to the fluid of low impedance as detailed herein and/or variations thereof. The foam can "wick" the fluid, thus converting the foam from a high impedance arrangement to a low impedance arrangement, whereby testing for an open circuit can commence. A sponge material can be used as well. This embodiment can provide control of the fluid within the package to a certain degree.

It is noted that in an exemplary embodiment, the inner surface 2227 of the foam 2225 (i.e., the surface that is configured to contact the electrodes 148) is not necessarily a smooth surface. In an exemplary embodiment, the surface 2227 is a non-smooth surface. In an exemplary embodiment, such a surface can have utilitarian value with respect to contacting electrodes 148 that are recessed within the support structure (e.g., a silicone support structure) of the array 146, or otherwise provide a relief area such that any compression of surface 2227 associated with one portion of the array is not transferred to another portion of the surface 2227. In an exemplary embodiment, the surface 2227 can be a corrugated surface or the like. The surface 2227 can have a cross-sectional profile in the form of a sinewave or a square wave or a saw wave (right triangles, pyramidal triangles, etc.). Any arrangement that can enable the teachings detailed herein and/or variations thereof to be practiced can be utilized in at least some exemplary embodiments.

Indeed, the aforementioned corrugation or the like can be utilized to concentrate the conductive material at the electrodes 148 of the electrode array 146. Corollary to this is an exemplary conductive apparatus 2223, depicted in FIG. 22B. There, the passageway through the conductive apparatus 2223 is lined with separate electrical contacts in the form of triangular-shaped contacts 2262, where the tube 2228 supporting the contacts 2262 is of a conductive material, thus placing the contacts into electrical conductive of the with each other.

In an exemplary embodiment, the configuration of conductive apparatus 2223 has utilitarian value in that it can enable the transition between testing for an open circuit and testing for a short circuit to be executed with minimal movement of the conductive apparatus 2223 relative to the electrode array 146. In this regard, FIG. 22C depicts the electrode array 146 located in the conductive apparatus 2223 in a configuration to enable testing for an open circuit, where conductors 2262 are in contact with each electrode 148, as can be seen. In an exemplary embodiment, by moving the conductive apparatus 2223 relative to the electrode array 146, and/or vice versa, the components can be locationally situated to enable testing for a short circuit, as can be seen in FIG. 22D, where the contacts 2262 only contact the silicone body of the array 146, which is of a relatively high impedance material. In this regard, a relatively minimal amount of relative movement (e.g., half the length between electrodes) between the pertinent components can be utilized to transition from testing for an open circuit to testing for a short circuit, and/or vice versa.

It is noted that while FIG. 22D discloses that the contacts are located in an evenly distributed manner, contacts can be spaced according to the location of the electrodes of the given electrode array under testing. That is, in some embodiments, the electrodes 148 are not evenly spaced, and thus the conductors are likewise not evenly spaced.

Figure 22B:
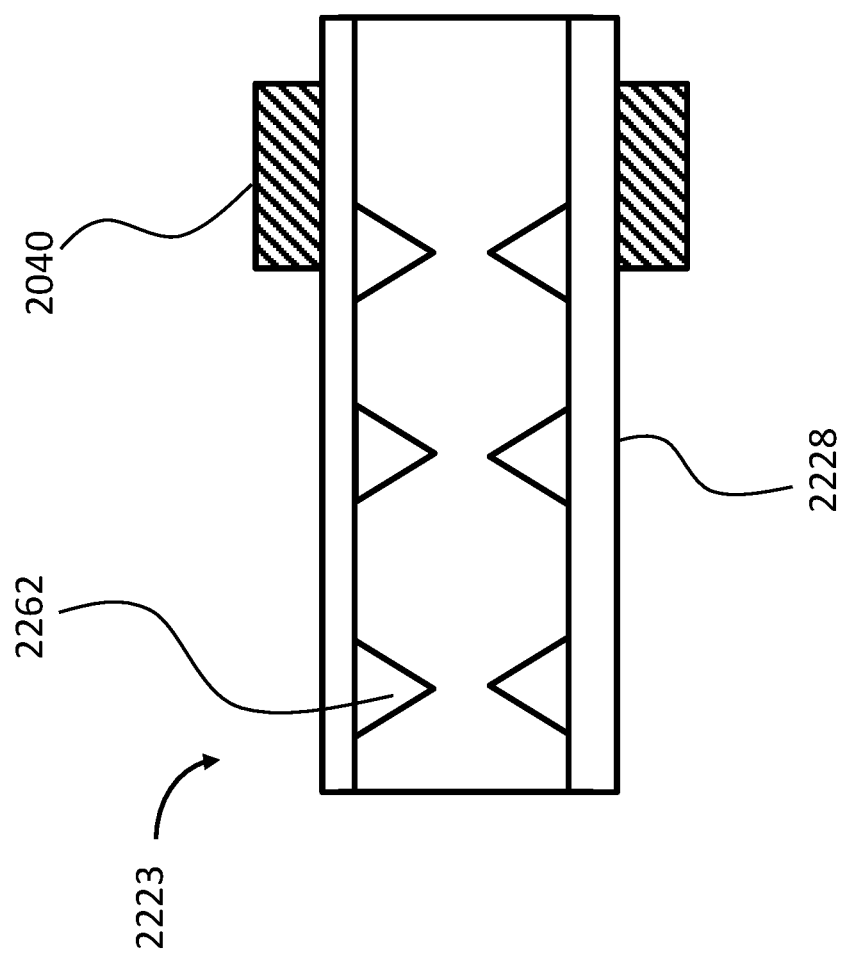
Figure 22C:
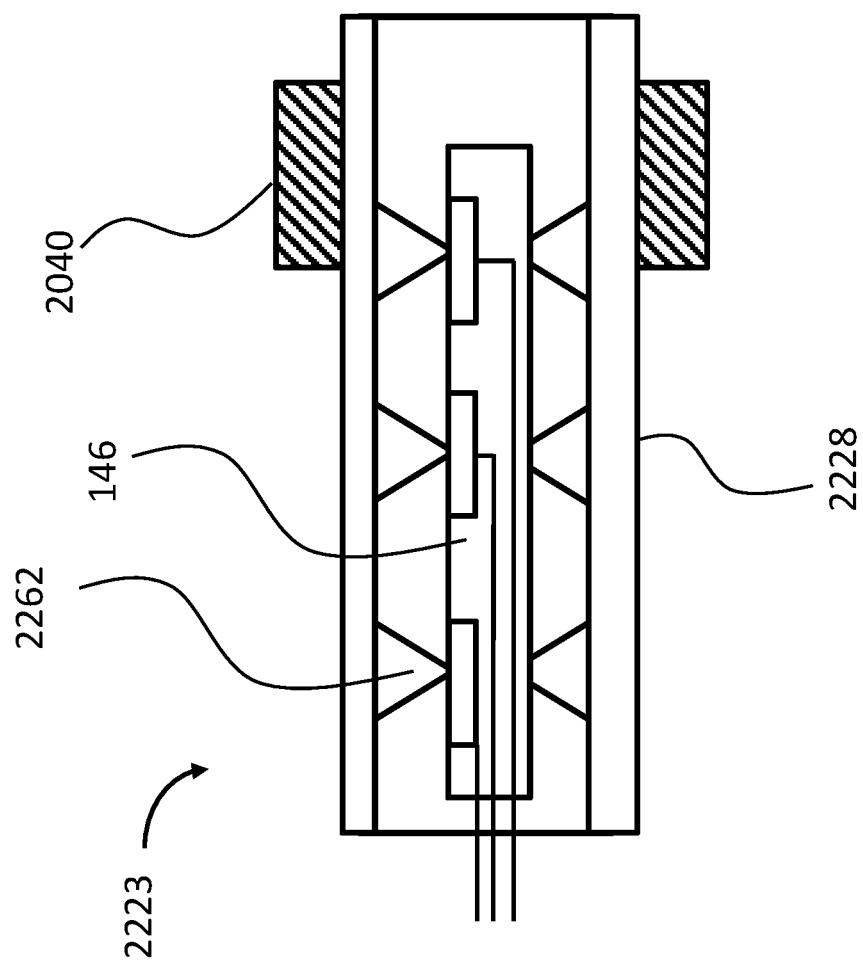
Figure 22D:
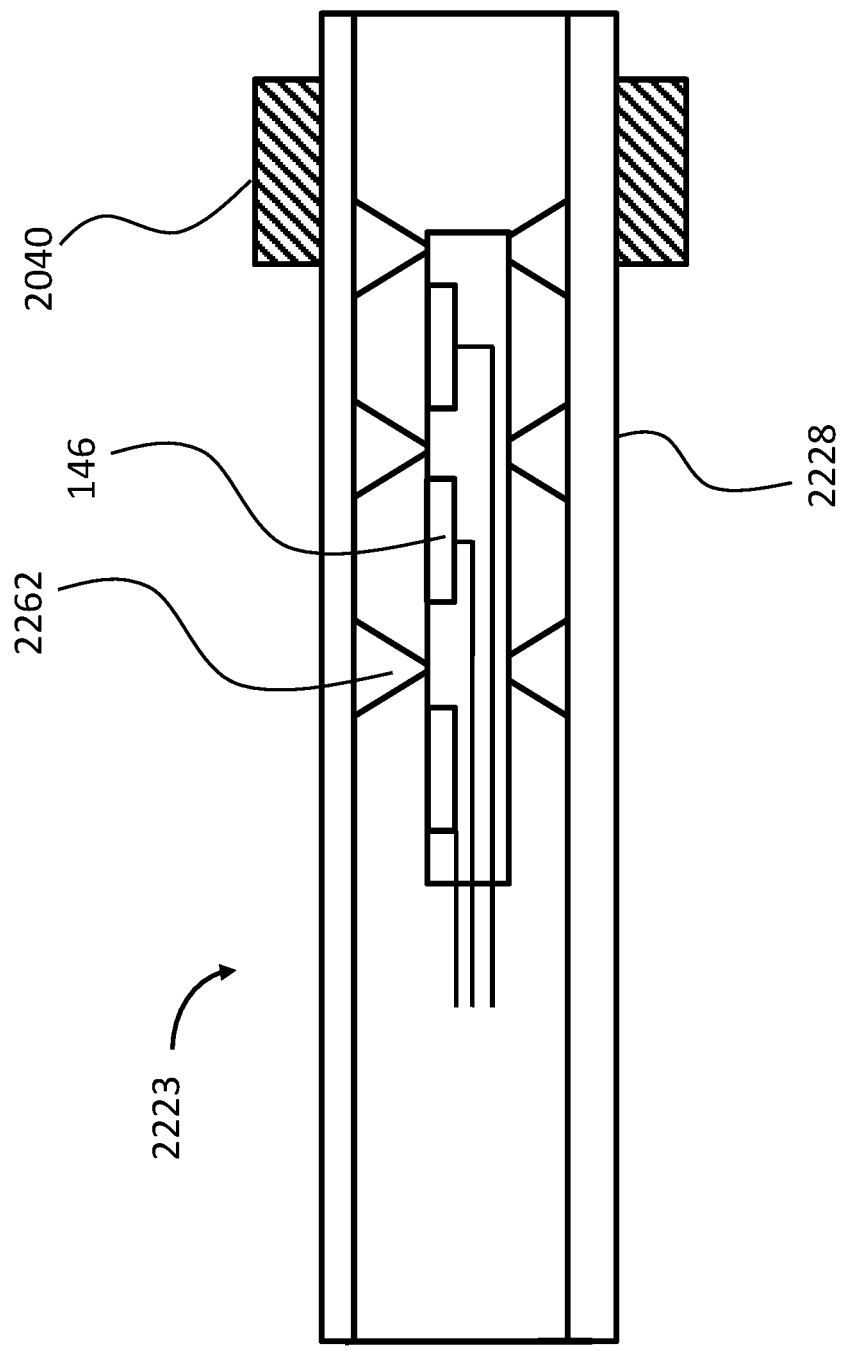

Is further noted that in an exemplary embodiment, the contacts 2262 can be configured to be compressible, at least with respect to the portions on the tip, as can be seen in FIGS. 22C and 22D relative to FIG. 22B. Alternatively and/or in addition to this, the contacts 2262 can be supported on a flexible material that flexes to provide space. The contact can also be spring loaded in another exemplary embodiment (more on this below).

Note further that in some exemplary embodiments, the concept depicted in FIG. 22B can be varied so as to enable transition from testing for an open circuit to testing for a short circuit to be implemented by rotating the conductive apparatus 2223 relative to the electrode array 146 and/or vice versa, in view of the fact that the electrodes of the electrode array 146 do not circumnavigate the outer periphery of the electrode array 146. That is, in an exemplary embodiment, the contacts 2262 do not extend all the way about the interior passage way of the conductive apparatus 622. For example, the conductors 2262 can be located only at the top of the conductive apparatus 2223, instead of all the way around, as is the case with the embodiment of FIG. 22E.

Figure 22E:
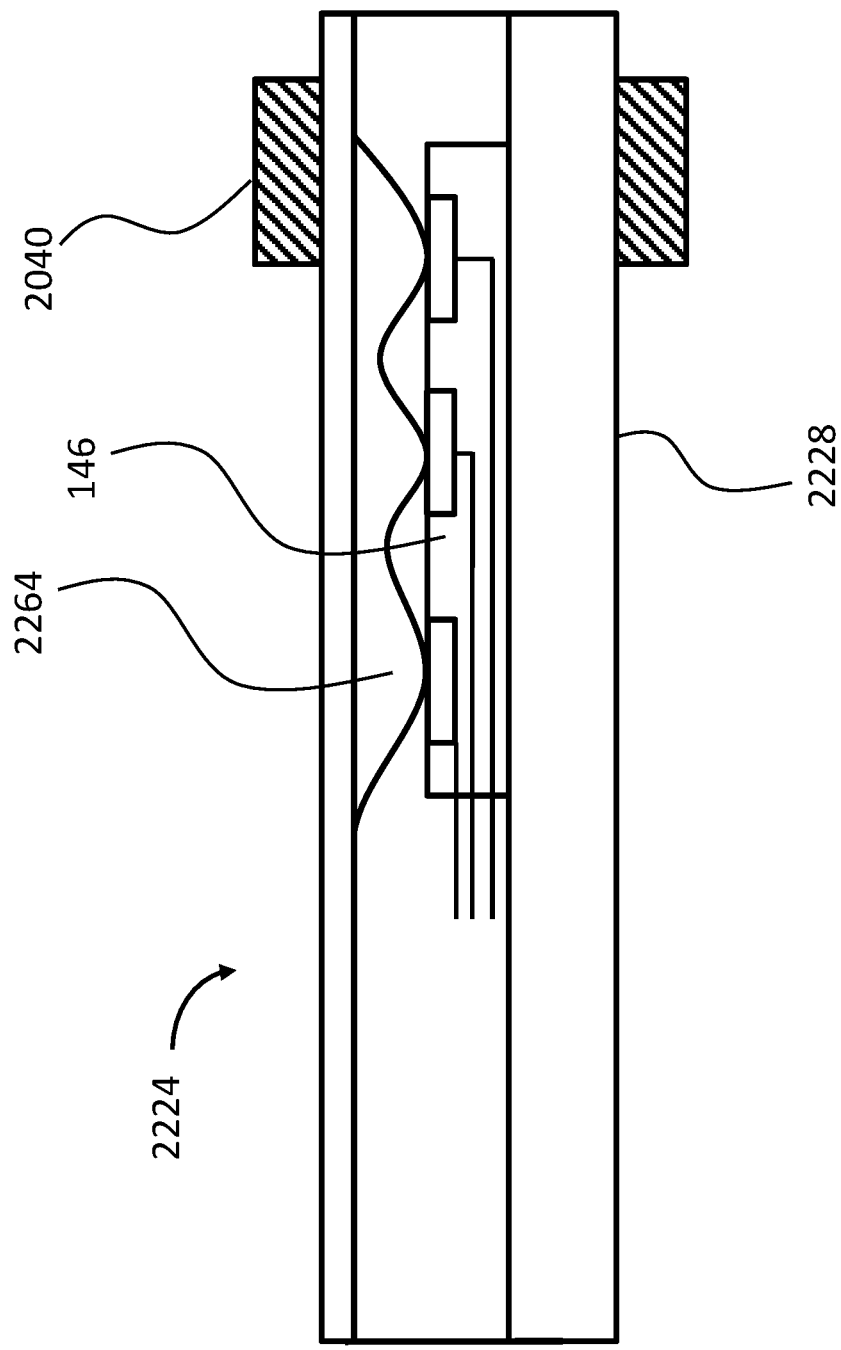

It is further noted that variations of the concept depicted in FIG. 22E can be implemented to enable the teachings detailed herein. Instead of utilizing triangular contacts as seen, square contacts can be utilized. Still further, undulating contact surfaces can be utilized such that the crests of each undulation are in phase with the respective electrodes (e.g., aligned with the centers of the electrodes) of the electrode array. The spacing of each crest/contact surface is such that movement of the electrode array relative to the conductive apparatus and/or vice versa takes the electrodes out of contact with the contacts in a manner concomitant with FIG. 22D. FIG. 22E depicts an exemplary embodiment of a conductive apparatus 2224 utilizing a "wavy" contact surface, where contact apparatus 2264 can be seen to have crests that are in phase with the electrodes of the electrode array 146.

Still further, the conductive apparatus can utilize a helicoil, or a spiral, as the contact apparatus, with spacings of the coil are set to correspond with the spacings of the electrodes.

Any arrangement of a contact apparatus that will enable the teachings detailed herein and/or variations thereof to be utilized can be utilized in some embodiments.

It is noted that while the embodiments depicted in the FIGs. tend to show a relatively large conductive apparatus relative to the electrode array 146, it is noted that in at least some exemplary embodiments, the conductive apparatuses are generally on the same size scale as the electrode array 146. In this regard, in an exemplary embodiment, the conductive apparatuses can be in the form of a cap or a sheath or the like that encapsulates the electrode array 146. Corollary to this is that the end of the cap could be closed, or, alternatively, open, as is depicted in the figures.

Figure 23:
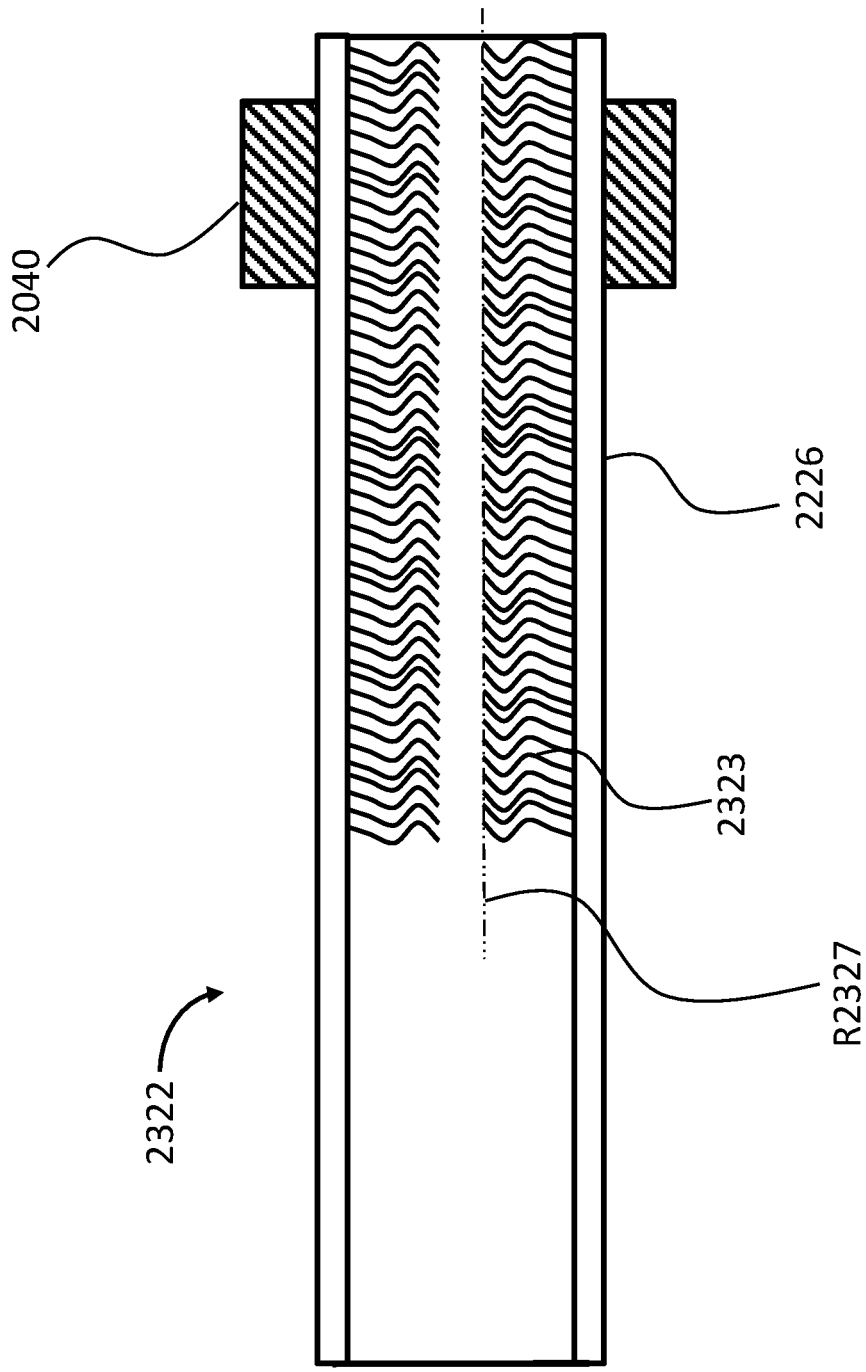

Note further, bristles and/or hair-like structures can be utilized in at least some exemplary embodiments for the electrode interface surface of the conductive apparatus 622. FIG. 23 depicts such an exemplary surface R2327 (represented by a reference line in view of the fact that the surface is made up of a plurality of portions) that is utilized in an exemplary conductive apparatus 2322. More specifically, as can be seen, hair-like follicles 2323 are arrayed about the interior of tube 2226. These are conductive elements, and the cilia are conductively linked to one another (for example, as a result of a dense pack, or as a result of the use of a conductive material of tube 2226 or another material inside the tube 2262). Alternatively and/or in addition to this, the tube 2226 can be a nonconductive material, and a binding agent that is conductive can be utilized to adhere the cilia like/hair-like follicles 2323 to the wall of the tube 2226, and if the binding agent extends between the roots of the follicles 2323, conductive the will be established between different follicles.

It is further noted that the configurations detailed herein can have sloped surfaces or otherwise guide services to assist in the insertion of an electrode array 146 into the passage inside the various conductive apparatuses detailed herein. To be clear, in an exemplary embodiment, the geometries detailed herein are exemplary geometries. Any configuration that will enable the teachings detailed herein and/or variations thereof to be practiced can utilize in at least some exemplary embodiments.

Figure 24:
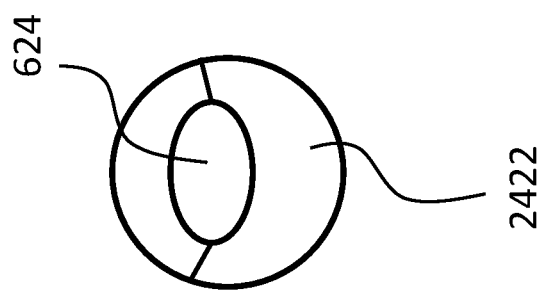

FIG. 24 depicts an exemplary alternate embodiment of a conductive apparatus 2422. In an exemplary embodiment of this exemplary embodiment, conductive apparatus 2422 is configured to spit apart upon manipulation through the package 410 by hand. In this regard, FIG. 24 depicts a view looking down the longitudinal axis of the conductive apparatus 2422, which corresponds in outer geometry to the conductive apparatus 622 detailed above. In an exemplary embodiment, the two portions of conductive apparatus 2422 are magnetically attracted to one another. The apparatus 400 is configured such that the two portions can be manipulated through the package 410 to variously place those two portions around the electrode array 146 to enable testing for an open circuit and/or to remove those two portions (or at least one portion, the one contacting the electrodes 148 of the electrode array 146) from the electrode array 146 to enable testing for a short circuit. Accordingly, in an exemplary method, apparatus 400 is obtained with the conductive apparatus 2422 surrounding or otherwise in contact with the electrodes electrode array 146. Testing for an open circuit is executed, and then the components of conductive apparatus 2422 are split apart from one another and moved via manipulation through the package 410 (which is a flexible package in some embodiments, made from plastic or the like in some embodiments). Testing for the short circuit is then commenced.

In an exemplary embodiment, a magnetic field can be utilized to move at least one component away from the other component.

Note further, in an alternate embodiment, the two components (or more components) can be mechanically held together via a quarter turn device or the like (half turn, eighth turn, etc.). In an exemplary embodiment, the apparatus 400 is configured such that the quarter turn device can be turned to unlock the two components from each other (which turning can be accomplished through the packaging 410 (by hand and/or using a magnetic field) and then the two components can be manipulated through the package 410 away from one another).

Figure 25A:
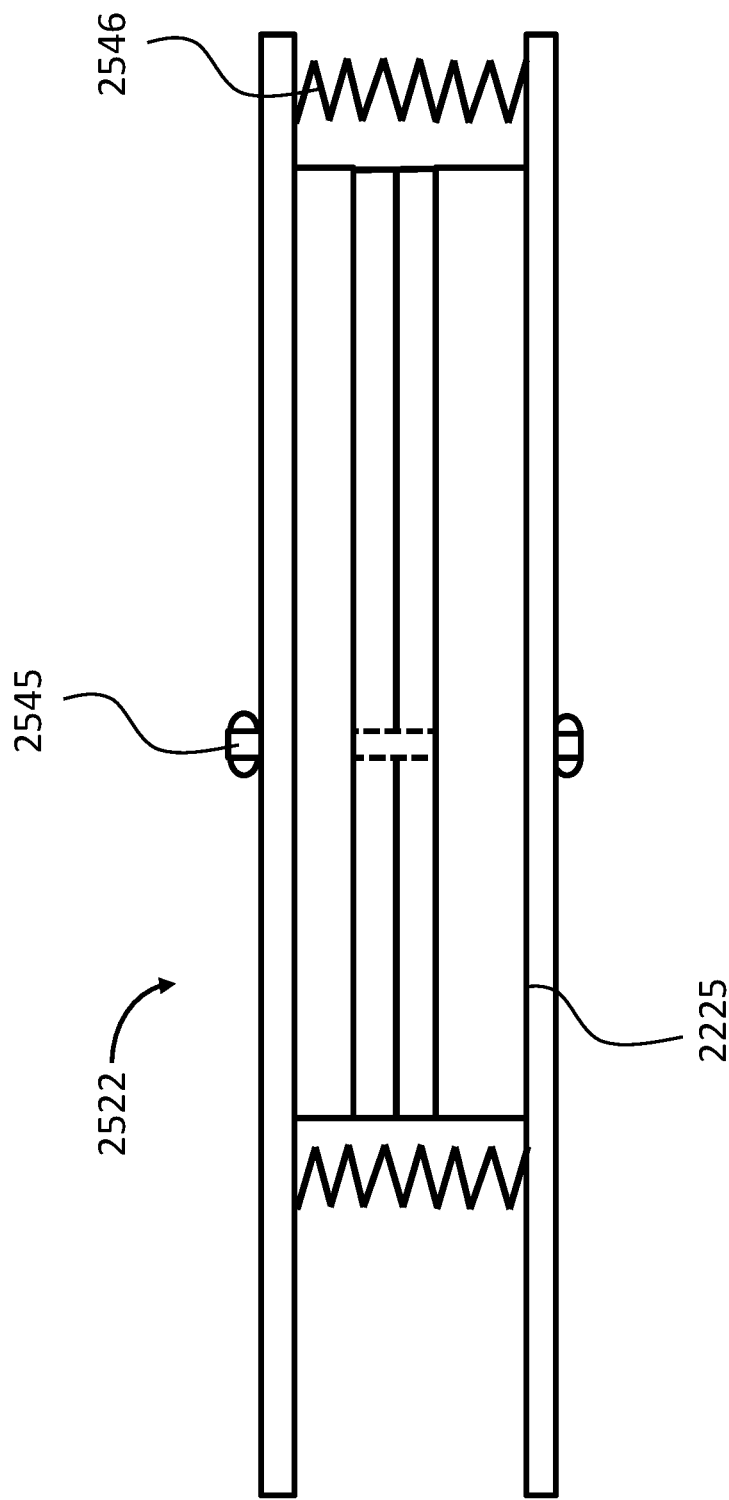
Figure 25B:
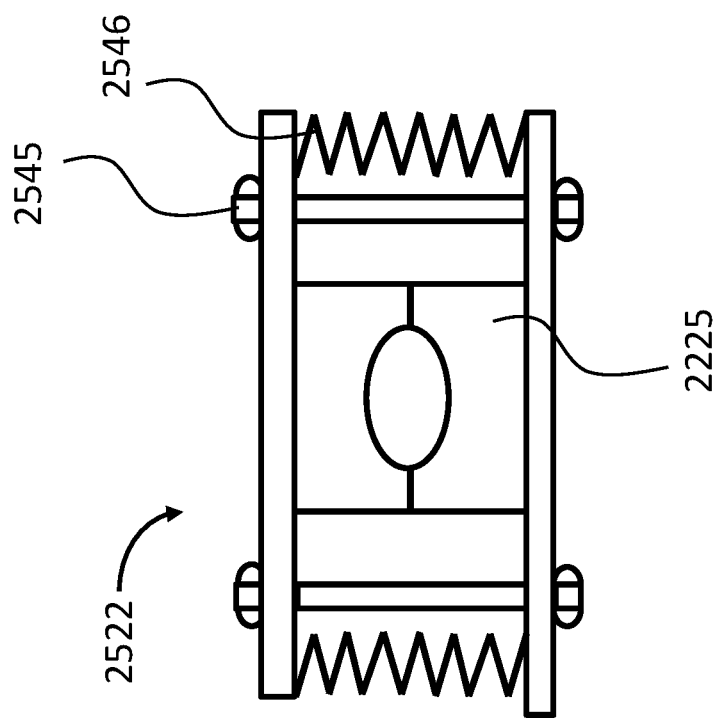

In an exemplary embodiment, a spring-loaded actuator can be included in the conductive apparatus to hold the components together. In an exemplary embodiment, the apparatus 400 is configured such that the user need only apply pressure and/or relieve pressure through the packaging 410 to actuate the actuator and release the two components from each other (e.g., the actuator could actuate a ball detente system that holds the two components together). Indeed, in an exemplary embodiment, the two components can themselves be spring-loaded such that upon the actuation of the actuator, the two components spring away from one another, thus freeing the electrode array 146 without manipulation through the package 410. In this regard, by way of example only and not by way of limitation, FIG. 25A depicts an exemplary conductive apparatus 2522, that includes springs 2546 that are loaded in compression such that a force is applied to the two components of the conductive apparatus 2522 to push those two components away from one another. These forces are resisted by ball detent apparatus 2545. If sufficient pressure is applied to the two portions of the conductive apparatus 2522 (or, if sufficient pressure is relieved, such as by moving the packaging walls away from one another), the ball detent system 2545 is actuated, and the two components are free to move away from one another, which movement is encouraged or otherwise forced due to the springs 2546. (It is noted that the device of FIG. 25A is presented in functional terms. The components depicted will be located out of the way of any electrode array 146 that could be located therein. In this regard, FIG. 25B depicts a side view of the conductive apparatus 2522 of FIG. 25 (e.g., a view looking from the left or right of FIG. 25A).)

With regard to the separable conductive apparatuses, it is noted that in some embodiments, only some of the interior surface is formed of the conductive material, while in other embodiments, all of the interior surface is formed of the conductive material. By way of example, the surfaces that contact the electrodes form a conductive surface, while at least some of the other surfaces do not so form a conductive surface. All of this said, this can be also the case with respect to the non-separable conductive apparatuses as well.

Corollary to the above is that in an exemplary embodiment, the conductive surface can be a tearoff strip or the like. That is, in an exemplary embodiment, the conductive apparatus 622 can be a multipart conductive apparatus, where only a portion of the interior surface is a conductive surface. After testing for an open circuit is completed utilizing the portion of the interior surface that is a conductive surface, a tearoff strip supporting that conductive surface can be removed by "tearing" the strip off of the other portions of the conductive apparatus, thus removing the conductive surface from contact with the electrodes, after which testing for the close circuits can be executed. In an exemplary embodiment, this can be implemented by a pull string or the like that extends from the tearoff strip to an exterior of the packaging, wherein the interior of the package 410 remains sterilely sealed even after the pull string is pulled. In this regard, a monofilament can extend from the tearoff strip through a seal in the packaging 410 to an exterior thereof, which monofilament can be pulled by the user to remove the tearoff strip.

Accordingly, in an exemplary embodiment, the apparatus 400 is configured to vary the impedance by manipulation of a conductive material into contact with and away from contact with an electrode of the electrode array.

In an alternative embodiment, the conductive apparatus 622 can be configured to shrink or expand, thereby alternately placing the electrodes into the requisite conductivity with each other and removing the electrodes from conductive to the with each other.

Still further, in an exemplary embodiment, the conductive apparatus 622 can be configured to deform or the like. In an exemplary embodiment, the conductive apparatus can be a single piece apparatus, but have a slit running along the longitudinal axis thereof, that can enable the conductive apparatus 622 to be deformed by external forces so as to move the conductive surface away from the electrodes.

Figure 26:
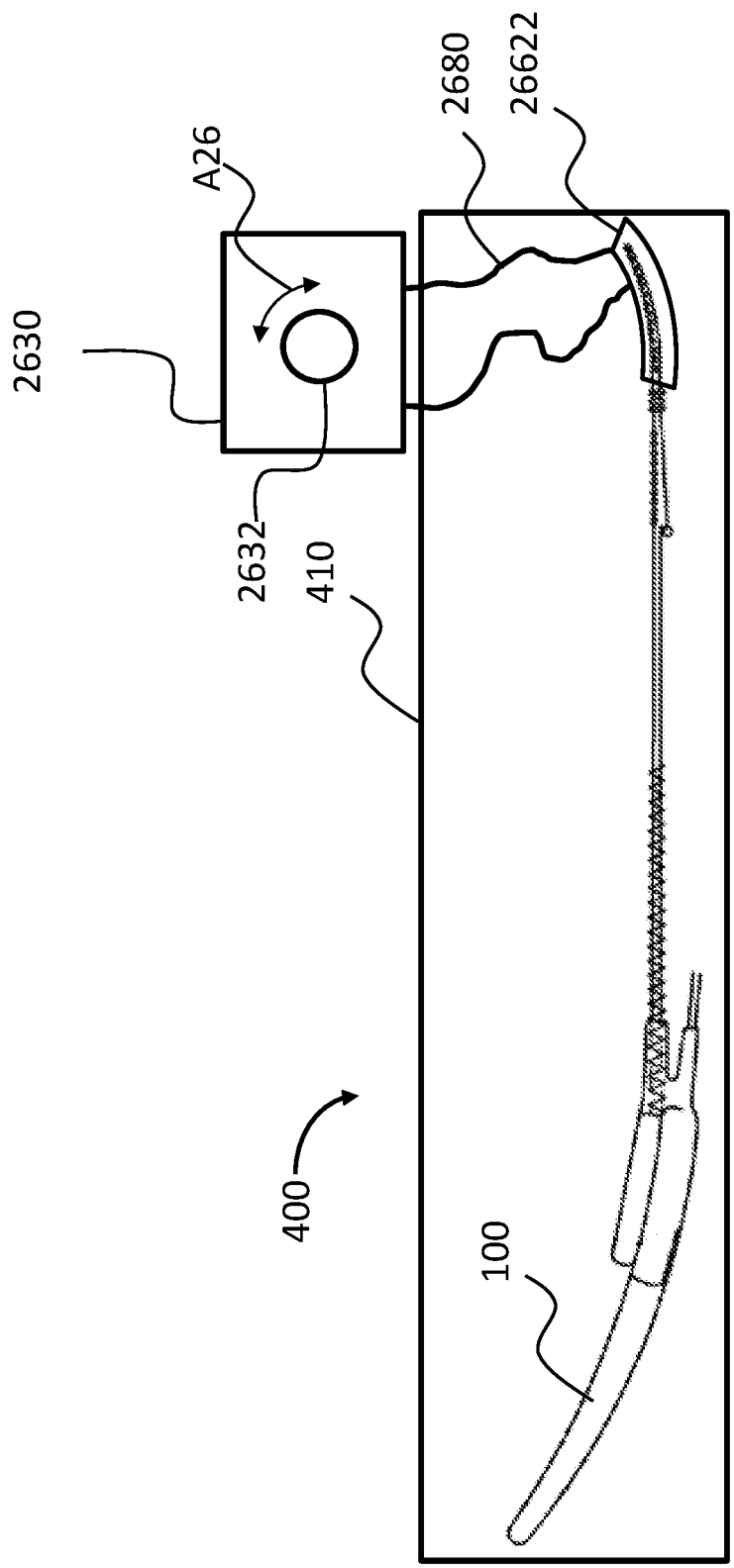
FIG. 26 is a schematic of another exemplary embodiment.
Figure 27:
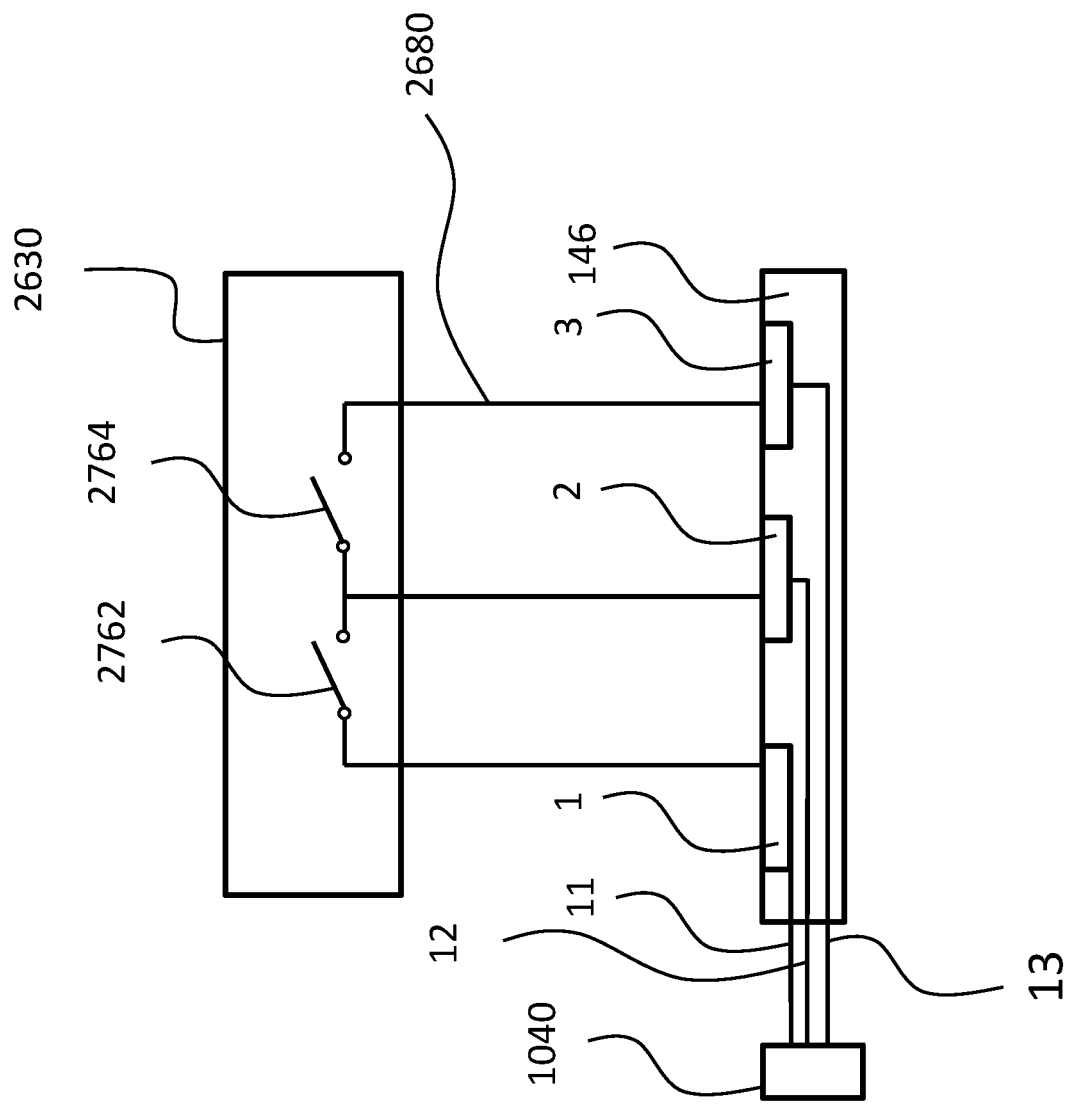
FIG. 27 is a functional schematic a principle of operation of the exemplary embodiment of FIG. 26.

Note further that in some exemplary embodiments, the impedance between electrodes can be varied without moving any components within the package 410 (fluidic or otherwise), at least in the global geographic sense. By way of example only and not by way of limitation, referring now to FIG. 26, there is an apparatus 400 that includes a conductive apparatus 26622 that is in electrical communication via lead assembly 2680 with a device 2630 that is located completely outside the package 410. In this exemplary embodiment, device 2630 is an impedance adjustment device that enables the impedance to be adjusted between the various electrodes 148 of the electrode array 146. This is functionally represented by adjustment knob 2632, which can be moved in the direction of the arrow A15 to adjust the impedance between two or more electrodes. Referring now to FIG. 27, there is a functional schematic of some of the portions of the apparatus 400 of FIG. 26, where only three electrodes are depicted for ease of disclosure (as with the embodiments above, the pertinent components can be duplicated for electrode arrays 146 that have additional electrodes, where in at least some exemplary embodiments, the array 146 includes 22 electrodes).

More specifically, as can be seen, the functional schematic of FIG. 27 depicts separate leads extending between each electrode of the array 146 and the device 2630. Device 2630 is depicted as including switches 2762 and 2764 that are configured to controllably place the respective leads into electrical communication with each other. In an exemplary embodiment, the adjustment knob 2632 (one or more can be used) controls the switches 2762 and 2764 (or one or more toggle switches or the like can be used) to be in the open and/or closed position. In an exemplary embodiment, multiple mobs 2632 are utilized, alternatively and/or in addition to this, toggle switches are presented. Any apparatus that can enable the switching of the switches 2762 and 2764 can be utilized at least some exemplary embodiments.

Accordingly, in an exemplary embodiment, the various switches are controlled to variously place electrodes into electrical communication with one another. In an exemplary embodiment, all of the switches can be closed during the testing for the open circuit, or each switch or a plurality of switches can be variously closed and open during the testing, where the various switches are variously closed depending on which circuit is being tested for an open circuit. In an exemplary embodiment, all of the switches can be open during testing for the short circuit, or each switch or a plurality of switches can be variously opened and closed during the testing, where various switches are variously open depending on which circuit is being tested for a short circuit.

In an exemplary embodiment, the lead assembly 2680 includes a feed-through apparatus at the boundary of the package 410 so as to maintain the sterile environment within the package 410. In an exemplary embodiment, device 2630 can be hooked to the lead assembly 2680 via an electrical connection apparatus (e.g., a serial port connector or any other suitable connector) that can be coupled and/or decoupled to the array 2680 to implement the testing detailed herein. Accordingly, in an exemplary embodiment, the device 2630 can be used for multiple different apparatuses 400 containing cochlear implants 100. That said, in an alternative embodiment, the device 2630 can be part of the apparatus 400, and each apparatus 400 shipped can include device 2630.

It is noted that the device 2630, in at least some exemplary embodiments, is a device that only adjusts the impedances between given electrodes. That is, it is not a test device per se, but instead a component that enables the impedance to be varied so that the test detailed herein can be executed.

Note that alternate variations of device 2630 can be utilized. Instead of switches 2762, rheostats can be used.

Note further that in an exemplary embodiment, the device 2630 can be located within the package 410. In an exemplary embodiment, a magnet or the like can be utilized to actuate the switches (individually or together). That is, in an exemplary embodiment, the switches can be linked to magnets located inside device 2630, and a magnet placed in proximity thereto, but on the outside of package 410, can move the magnet(s) attached to the switches, and thus move the switches, opening and/or closing the circuit(s) depending on how the magnet inside the package 410 is moved. Still further, in an exemplary embodiment, a component inside the package 410 can be manipulated through the package wall that opens and/or closes the switches. Still further, by way of example only and not by way limitation, in an exemplary embodiment, the switches can be linked to a movable mass that moves with movements of the package 410 in a given orientation. For example, holding the package 410 such that the electrode array 146 is located closer to the ground, and thus the receiver/stimulator 180 is located further from the ground, in at least a generally vertical direction, can move a mass located in the package 410 to move the switches to an open location, where gravity pulls that mass in that direction to open the switches. Then, the package 410 can be held such that the electrode array 146 is located further from the ground, and thus the receiver/stimulator 180 is located closest to the ground, again in at least a generally vertical direction, which can move the mass located in the package 410 to move the switches to a close location, where gravity pulls the mass in that direction to close the switches.

It is noted that the movable mass can be utilized with other embodiments, such as the embodiment that moves the conductive apparatus relative to the electrode array.

Any arrangement that can enable the opening and/or closing of the switches to implement the teachings detailed herein can be utilized at least some exemplary embodiments.

Note further that in an exemplary embodiment, elements 2762 and 2764 can be transistors or the like. Indeed, in an exemplary embodiment, the device 2630 can be located in the package 410, and can include a power source. This power source can be used to actuate the transistors, which can be utilized to open and/or close the circuits. In an exemplary embodiment, the device 2630 can be activated to enable the transistors by applying pressure to an on/off switch that can be actuated through the material of the package 410 (indeed, such switching can be utilized as the switches 2762 and 2764 in some embodiments). In an exemplary embodiment, the device 2630 can be activated to enable the transistors by shaking the package 410 and/or by activating a magnetically controlled switch utilizing a magnet external to the package 410.

Still further, by way of example only and not by way of limitation, device 2630 can include an automatic feature that automatically controls the opening and/or closing of the various switches (or the adjustment of the rheostats, etc.). Still further, device 2630 can have its own inductance coil such that the device can 2630 can communicate with an external component that controls the switching of the switches and/or the adjustment of the rheostats external to the package 410, which controls are communicated via the inductance system to device 2630. Other communication arrangements can be utilized in at least some exemplary embodiments.

It is noted that in an exemplary embodiment, the conductive apparatus and device 2630 can be an integrated unit. In an exemplary embodiment, this can be achieved via the use of MEMS technology and/or transistors.

Note further that while the above exemplary embodiment was disclosed as having a power source, such as a battery, located in packaging 410, in an alternate embodiment, power can be inductively transferred from the outside of the package 410 to the inside of the package 410. Accordingly, in an exemplary embodiment, the system 400 includes an inductance coil located within package 410, configured to be exposed to an inductance field from outside the package 410. The system 400 is configured to capture the inductance field utilizing the inductance coil located within package 410, and utilize that to power the device 2630 or any other component located in package 410 that can enable the teachings detailed herein and/or variations thereof.

It is noted that any arrangement that can enable the teachings detailed herein and/or variations thereof to be practiced can be utilized in at least some embodiments. The various electrical properties detailed herein can be achieved in any manner that can enable those electrical properties to be utilized according to the teachings detailed herein. With respect to placing two or more electrodes into conductivity with one another, the aforementioned impedances, etc., can be achieved utilizing the general material of the given conductive apparatus (e.g., what the entire conductive apparatus is made from, or at least what most of the conductive apparatus is made from), or can be achieved utilizing a doped system and/or a system where only the pertinent portions are coated with the material that can allow the aforementioned impedances and/or electrical properties to be achieved to implement the teachings detailed herein. By way of example only and not by way limitation, passage 624 of conductive apparatus 622 can be coated with a conductive material, while the remainder of conductive apparatus 622 can be a nonconductive material.

Figure 28:
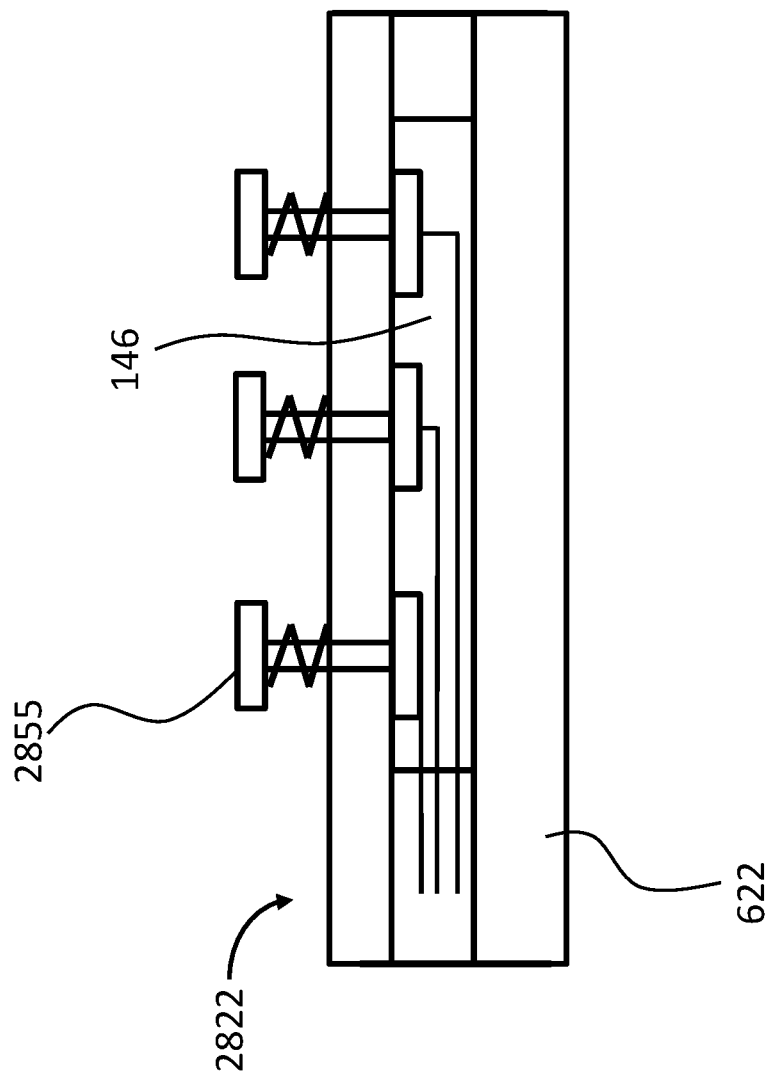
FIG. 28 is a schematic of another exemplary embodiment of a conductive apparatus.

FIG. 28 depicts yet another alternate embodiment of a conductive apparatus 2822, utilizing spring-loaded plunger pins 2855 to vary the connectivity between the electrodes. In an exemplary embodiment, each individual plunger pin 2855 can be moved upward and/or downward to alternately contact/disconnect the electrodes 148 of the electrode array 146.

Figure 29:
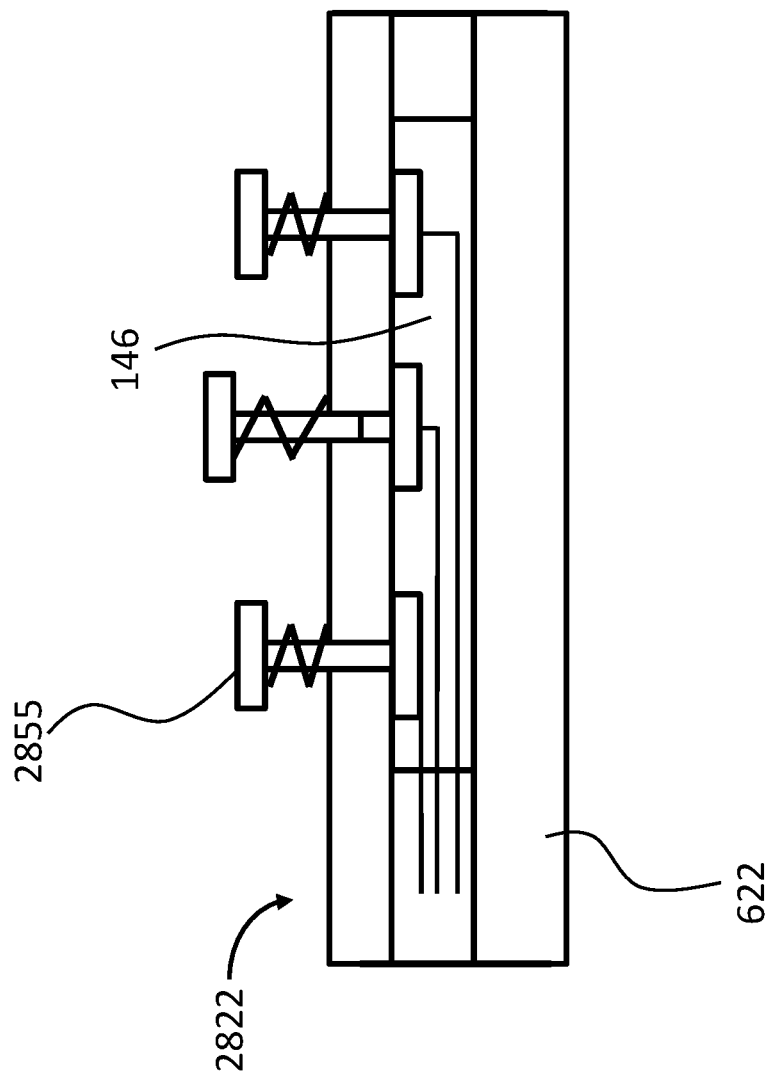
FIG. 29 is a schematic of the apparatus of FIG. 28 in use.

In an exemplary embodiment, each individual plunger pin 2855 can be moved relative to one another. In another embodiment, the plunger pins can be linked to one another such that all plunger pins move. The former embodiment can be utilized during methods of testing for an open circuit where a specific open circuit is sought to be identified (as opposed to just the general concept of determining that there exist in open circuit). FIG. 29 depicts an exemplary scenario of use where only two of the plunger pins 2855 are in contact with the respective electrodes. In an exemplary embodiment, due to the spring loading of the plunger pins 2855, the pins 2055 can be actuated via manipulation through the package material 410 (e.g., pressure can be applied through the material of package 410 to actuate the plunger pins 2855).

Still further, in an exemplary embodiment, all of the plunger pins 2855 can be linked to one another such that actuation of one pin actuates all pins.

In view of the above, it can be understood that in an exemplary embodiment, the apparatus 400 is configured such that the impedance between electrodes can be varied. In an exemplary embodiment, the impedance can be varied from a relatively low impedance to enable testing for an open circuit (e.g., 500 ohms or less) to a relatively high impedance to enable close circuit testing (e.g., 30,000 ohms or more). In an exemplary embodiment, the impedance can be varied from any value or range of values that can enable the teachings detailed herein.

Accordingly, in an exemplary embodiment, the apparatus 400 is configured to alternately provide and eliminate electrical conductivity between two or more electrodes.

Figure 30:
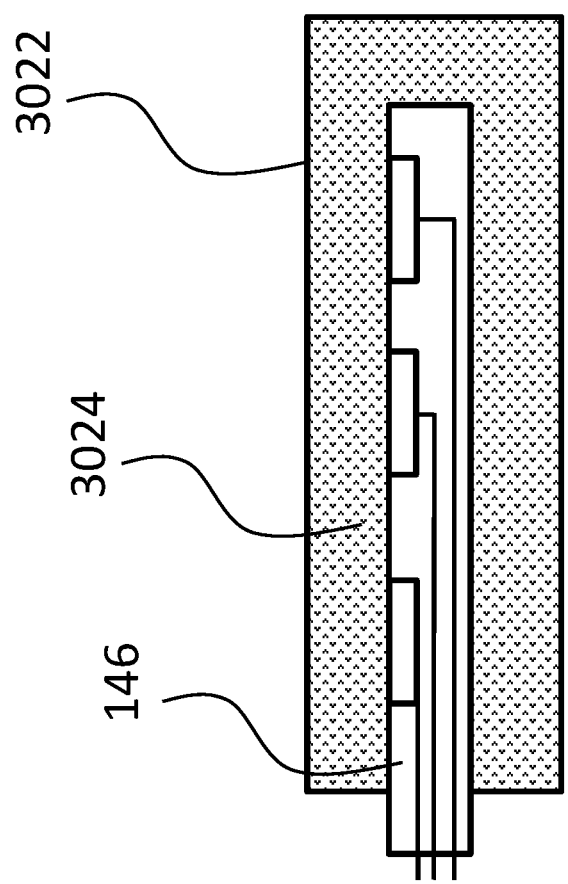
FIG. 30 is a schematic of another exemplary embodiment of a conductive apparatus in use.

As noted above, not all embodiments utilize the varying impedance feature. In some embodiments, a controlled/fixed impedance is utilized. As detailed above, in an exemplary embodiment, such utilizes ohms law or any other principle of electrical engineering to enable testing for an open circuit and testing for a short circuit to be executed utilizing the given controlled impedance. In an exemplary embodiment, a foam spiked or otherwise including a conductive material of known impedance is utilized. In an exemplary embodiment, a conductive liquid or the like can be utilized. In this regard, the conductive apparatus 622 can be a cap or the like that holds a fluid therein along with the electrode array 146 in a sealed manner relative to the remainder of the electrode array assembly 190. By way of example only and not by way limitation, referring now to FIG. 30, in an exemplary embodiment, there is a conductive apparatus 3022 in the form of a cap, where the electrode array 146 is located at least partially therein (e.g., at least the portion that has the electrodes is located in the cap). In an exemplary embodiment, the conductive apparatus 3022 includes a conductive fluid 3024 of a known type and quantity to establish a known impedance between the electrodes. In an exemplary embodiment, the apparatus 400 is shipped with the electrode array 146 located in the conductive apparatus 622, with the electrodes 148 exposed to the fluid 3024 at all times. That said, in an alternate embodiment, the blister packs detailed herein and/or other methods can be utilized so as to place the electrodes into contact with the fluid, which fluid is utilized for both testing for an open circuit and testing for a short circuit. That is, the fluid can be maintained away from the electrode array until testing commences.

In an exemplary embodiment, the fluid 3024 is a concentration of saline having a known impedance, or at least a concentration of saline utilized in the pertinent amounts to result in a known impedance with respect to the given electrode arrays 146 utilized there with.

In an exemplary embodiment, the electrical conductivity established between the electrodes is between 200 ohms and 4.7 megahoms.

Figure 31:
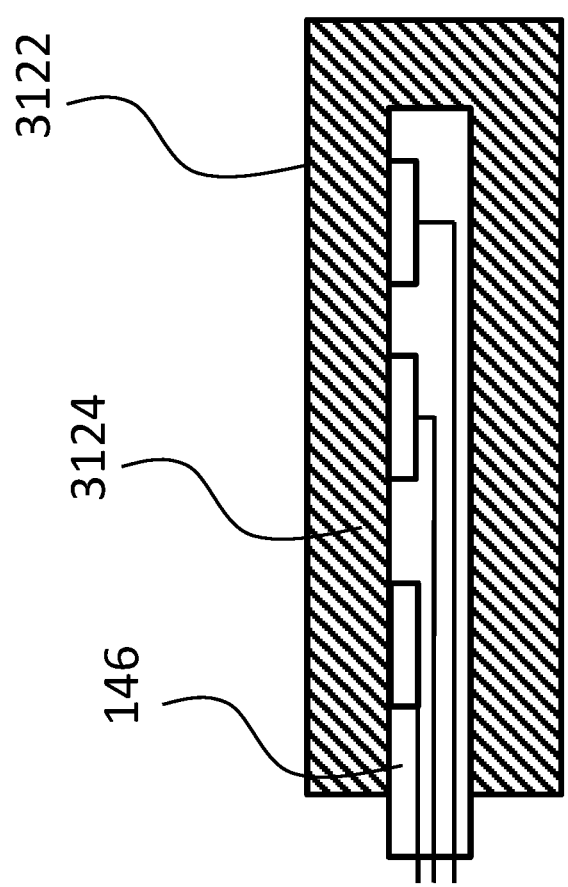
FIG. 31 is a schematic of another exemplary embodiment of a conductive apparatus in use.

That said, it is noted that in an exemplary embodiment, the impedance that is utilized for the testing of an open circuit and/or for testing of a short circuit is such that the impedance is discernibly different than the impedance of the leads connecting the electrodes. In an exemplary embodiment, the impedance of the leads is about 100 ohms, 200 ohms, 300 ohms or more (or less). In an exemplary embodiment where a given lead has an impedance of 100 ohms, the combined impedance of the circuit would be 200 ohms (each lead adding 100 ohms to the total impedance of the circuit). Again, as noted above, solids can be utilized to establish the electrical conductivity between the electrodes. FIG. 31 depicts an exemplary conductive apparatus 3122 that utilizes a foam 3124 that establishes an impedance between the electrodes of a known amount. As with the embodiment of FIG. 30, the conductive apparatus 3122 is in the form of a cap. The conductive apparatus 3122 can be utilized to test for both an open circuit and a short circuit. As with an exemplary embodiment of the conductive apparatus 3022, in an exemplary embodiment, the conductive apparatus 3122 is shipped in the packaging 410 in contact with the electrodes of the electrode array 146, and remains in contact until after testing for an open circuit and testing for a short circuit is executed.

Figure 32:
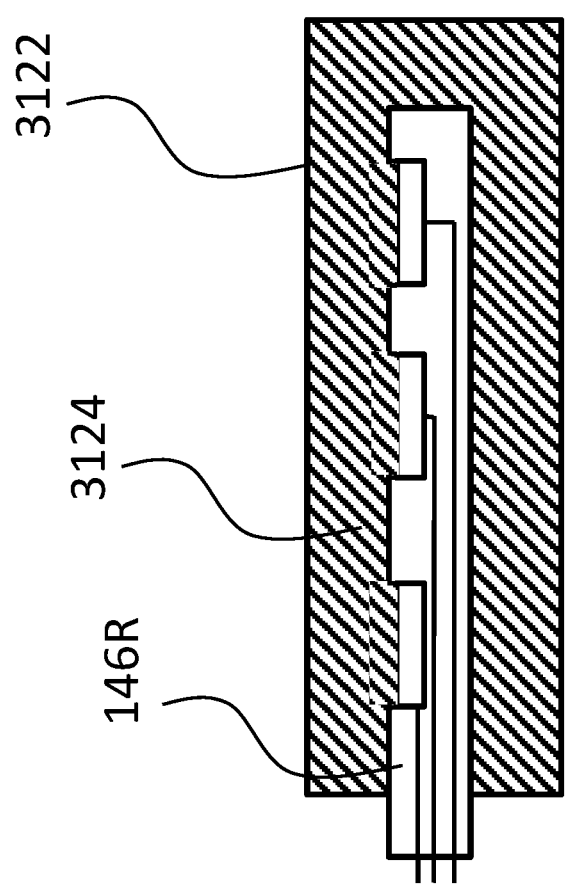
FIG. 32 is a schematic of another exemplary embodiment of a conductive apparatus in use.

In at least some exemplary embodiments, the teachings detailed herein and/or variations thereof can be utilized with the electrode arrays that have so-called recessed electrodes. In this regard, FIG. 32 depicts an exemplary electrode array 146R, having such electrodes, located in conductive apparatus 3122. As can be seen, the foam 3124 contacts each of the electrodes. In this regard, the larger diameter portions of the electrode array 146R compressed the foam 3124 just a bit more than that which is the case (if such is even the case) with respect to the portions of the electrode array 146R that are recessed.

It is noted that in at least some exemplary embodiments, the fluidic embodiments also can enable the testing for an open circuit in electrode array utilizing recessed arrays. Note further, by way of example only and not by way limitation, the undulating conductive contacts and/or the hair-like contacts detailed above can also be utilized with recessed electrodes. Any arrangement that can enable testing for an open circuit with respect to an array that utilizes recessed electrodes can be utilized in at least some exemplary embodiments.

Corollary to the embodiments of FIGS. 31 and 32, is that in some embodiments utilizing foam to contact the electrodes, while there will be some compression, the compression is such that the electrode array 146 is not damaged. In this regard, in an exemplary embodiment, the apparatus 400 is configured such that there is compression on the electrode arrays, but the compression that is utilized to enable testing for an open circuit does not damage the arrays (e.g., the arrays remain in a condition for implantation in a recipient). Still further, in an exemplary embodiment, there is a method that entails squeezing the conductive apparatus so as to place the conductors into contact with the electrodes of the electrode array 146 so as to enable testing for an open circuit, and then releasing the pressure to test for a short circuit.

It is noted that in at least some exemplary embodiments, there is utilitarian value with respect to the maintenance of a constant contact with the pertinent electrodes that are utilized for a given test. Accordingly, in an exemplary embodiment, the apparatus 400 is configured to maintain a constant contact with one or more or all of the electrodes during the testing for an open circuit. Still further, in an exemplary embodiment, the method detailed herein relating to testing for an open circuit entails testing for such while the conductive material of the conductive apparatus is in constant contact with the pertinent electrodes.

While the teachings above have at least sometimes been directed towards a so-called straight electrode array 146, in an exemplary embodiment, the teachings herein and/or variations thereof are applicable to a curved electrode array (i.e., a pre-curled electrode array, where the electrode array curls when unconstrained). That is, in an exemplary embodiment, the apparatus 400 is such that the cochlear implant 100 therein has a straight electrode array 146, and in some other exemplary embodiments, the apparatus 400 is such that the cochlear implant 100 therein has a curved electrode array. That is, in at least some exemplary embodiments, in some instances, the cochlear implant 100 is shipped in the packaging 410 such that the electrode array is in the straight orientation, and in other instances, the cochlear implant 100 is shipped in the packaging 410 such that the electrode array is in the curved orientation. (It is noted that a curved electrode array can be shipped/maintained in apparatus 400 in the straight orientation, and a straight electrode array can be shipped/maintained in apparatus 400 in a curved orientation, and visa versa.)

Accordingly, in an exemplary embodiment, the apparatus 400 includes a cochlear implant 100, wherein the electrode array as a curved electrode array. In an exemplary embodiment, the curved electrode array is in the curved orientation. In an exemplary embodiment, the electrode array of the cochlear implant 100 in the packaging 410 is curved to subtenant an angle of at least 360° (FIG. 2 depicts such an array in such a curved orientation). In at least some exemplary embodiments, one or more or all of the method actions detailed herein and/or variations thereof are executed with the electrode array in a curved orientation, such as a curved orientation where the electrode array is curved to subtenant an angle of at least 360°. Corollary to this is that in an exemplary embodiment, one or more or all of the apparatuses described herein and/or variations thereof are configured to implement the teachings detailed herein within electrode array that is in a curved orientation, such as an electrode array that is curved to subtended angle of at least 360°.

By way of example only and not by way limitation, in at least some exemplary embodiments, the fluidic teachings detailed herein can be utilitarianly utilized to enable testing for an open circuit of an electrode array in a curved orientation. Still further by way of example only and not by way limitation, the undulating contact surface detailed above can be utilized to enable testing for an open circuit of an array in a curved orientation. Still further, the aforementioned spiral/helicoil arrangement of contact(s) can be utilized with the electrode array in a curled orientation, at least in some embodiments. Still further, the conductive apparatus is that utilize foam can be utilized to enable testing for an open circuit while the array is in a curled orientation.

In at least some exemplary embodiments, the conductive apparatus has a hollow path corresponding at least generally to that of a mammalian cochlea, and is utilized to implement some of the teachings detailed herein with respect to an electrode array in the curved orientation. In an exemplary embodiment, the hollow path is established by two or more separate components, when joined together forming the hollow path. The electrode array 146 is placed in the hollow portion of one of the components such that it is in any of the curved orientations detailed herein and/or variations thereof, and then the other portion is placed over the portion that is supporting the electrode array 146 to maintain the electrode array in the curved orientation. In an exemplary embodiment, at least a portion of the hollow path includes the conductive features detailed herein and/or variations thereof.

In an exemplary embodiment, the conductive apparatus 622 is a curved tube, such as a curled tube (which, as with the other embodiments detailed above, can be integrated into the package 410), which maintains the curvature after the cochlear implant 100 is sealed in the packaging 410 and at least until the packaging 410 is opened. Note further that in an exemplary embodiment, the electrode array 146 can be inserted into the hollow path (e.g., the inside of a tube) in a manner analogous to insertion of the electrode array into a mammalian cochlea, and subsequently packaged in package 410 to establish the sterile environment. It is noted that a straight electrode array can be shipped or otherwise stored in the packaging 410 in the curved orientation and a curved electrode array can be shipped or otherwise stored in the packaging 410 in the straight orientation.

Figure 33:
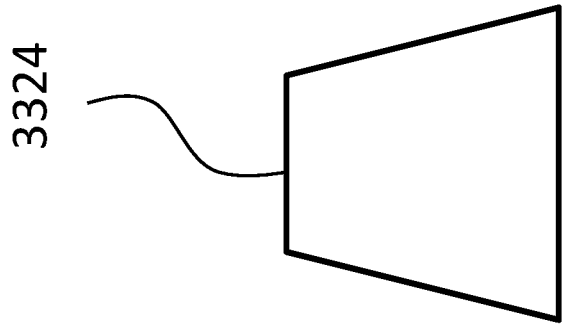
FIG. 33 is a schematic of another exemplary embodiment of a conductive apparatus.

That said, in at least some exemplary embodiments, a hollow path is not utilized. By way of example only and not by way of limitation, a truncated conical structure (or full conical structure) can be utilized, where the electrode array wraps around the cone, with the proximal end of the electrode array is located at the lower (wider) portions of the cone, and the distal end of the electrode array is located at the upper (narrower) portions of the cone. FIG. 33 depicts an exemplary side view of such a conical structure in the form of cone 3324. In an exemplary embodiment, at least the outer surface of the cone 3324 is made of a conductive material concomitant with the teachings detailed herein and/or variations thereof.

Figure 34:
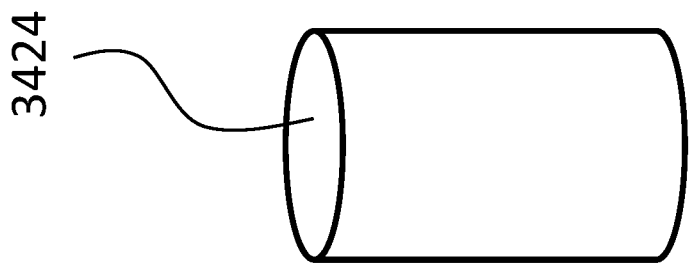
FIG. 34 is a schematic of another exemplary embodiment of a conductive apparatus.

That said, in an alternate embodiment, a cylindrical device, such as cylinder 3424, as seen in FIG. 34, can be utilized, where the outer surface of the cylinder 3424 is made of a conductive material concomitant with the teachings detailed herein and/or variations thereof.

In an exemplary embodiment, an outer sheath or cover or holder can be placed over the electrode array while the electrode array is wound about the cone and/or cylinder, so as to hold the electrode array in the curved orientation and in contact with the outer surface of the cone or cylinder (such that the electrodes are held in contact with the surface). In an exemplary embodiment, a clamp can be located over or otherwise around the electrode array after it is wound about the cylinder or cone. Indeed, in an exemplary embodiment, a clamshell apparatus can be placed around the wound electrode array. The clamshell apparatus can be made of a foam material, or at least have an interior lined with foam. Note further that the cone and/or cylinder and/or the device having the hollow passage generally corresponding to that of a mammalian cochlea, can be made of foam, or at least can have an outer (or inner surface with respect to the latter) made of foam.

Figure 35:
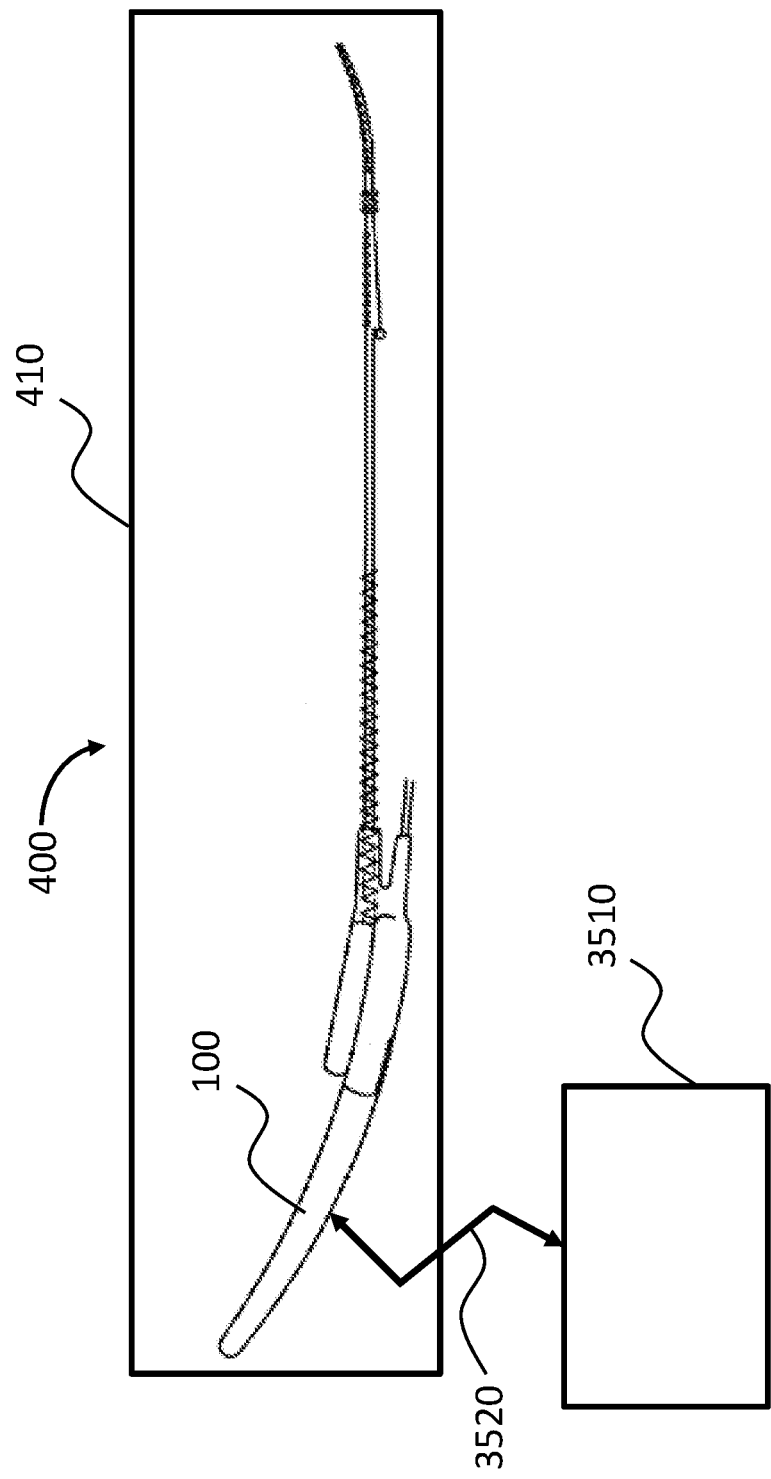
FIG. 35 is a schematic of an exemplary test apparatus in communication with an exemplary cochlear implant sterilely sealed within packaging from the outside according to an exemplary embodiment.

Referring now to FIG. 35, it can be seen that an apparatus 400 is in inductance communication via the inductance link 3520 with a cochlear implant array test apparatus 3510. In an exemplary embodiment, the test apparatus 3510 is a conventional cochlear implant test array apparatus that is usable to test for open circuits and/or for short circuits. In an exemplary embodiment, the apparatus 3510 is configured to communicate with the cochlear implant 100 via link 3520 in a manner that is the same as, or at least analogous to how, the external component 142 of the system 10 communicates with the implantable component 100 (i.e. the cochlear implant 100). By way of example only and not by way limitation, via link 3520, the apparatus 3510 generates an inductance signal that is received by the coils of cochlear implant 100. In an exemplary embodiment, instead of the inductance signal traveling through skin of the recipient, the inductance signal travels through the material of the package 410. Note further that in an exemplary embodiment, instead of or in addition to generating the inductance signal, the test apparatus 3510 receives an inductance signal that is generated by the cochlear implant 100 that is communicated through the material of the package 410. In at least some exemplary embodiments, the received signal contains telemetric data generated or otherwise outputted by the receiver/stimulator 180 of the cochlear implant 100. This telemetric data is data that is indicative of the presence and/or absence of an open circuit where there should be a short circuit and/or a short circuit where there should be an open circuit as a result of the testing detailed herein and/or variations thereof.

Briefly, it is noted that the test apparatus 3510 and/or the cochlear implant 100 are configured to implement testing for the open circuits and/or close circuits in a manner that is analogous to and/or the same as current test routines utilized by Cochlear Ltd. of Australia to test cochlear implants made by Cochlear Ltd. of Australia. Indeed, in an exemplary embodiment, the test apparatus 3510 is a test apparatus obtainable from Cochlear Ltd. of Australia, or any other vendor that produces a test apparatus that can enable the teachings detailed herein and/or variations thereof to be practiced.

More specifically, the test apparatus 3510 is configured to communicate with the cochlear implant 100 through the material of the package 410 to initiate testing routines to test for an open circuit and/or test for a short circuit. In an exemplary embodiment, these test routines are stored within the cochlear implant 100. That is, the test apparatus 3510 initiates the testing routines via the transpackage link 3520. That said, in an alternate embodiment, the cochlear implant 100 is configured to initiate the testing routines in the absence of direct instruction from the test apparatus 3510. Alternatively and/or in addition to this, the test apparatus 3510 is configured to essentially operate the cochlear implant 100 in a slave mode, with the test apparatus 3510 being the master, where the test apparatus 3510, via the link 3520, controls each step of the testing. Indeed, in at least some exemplary embodiments, this is the case with respect to the so-called partially implantable hearing prostheses, where the control apparatus (e.g. sound processor) is located in the external component of the system 10. Any arrangement that can enable the testing detailed herein and/or variations thereof can be utilized at least some embodiments.

In an exemplary embodiment, upon initiation of testing, the receiver/stimulator generates electrical signals that are transmitted via the electrical leads to (or at least towards, in the case of an open circuit) at the electrodes. In an exemplary embodiment, the cochlear implant 100 is configured to provide predetermined voltages and/or currents. The receiver/stimulator is further configured to receive a signal from the electrodes via the electrical leads. Again, in an exemplary embodiment, the receiver/stimulator is functionally analogous to the current generator/detector 1040 detailed above. In at least some exemplary embodiments, the receiver/stimulator is configured to evaluate the signal received from the electrode(s) and/or evaluate the fact that no signal was received from the electrode(s) via a given lead or leads, and evaluate these facts to determine whether or not an open circuit and/or a short circuit is present. This evaluation is conveyed via link 3520 to the test apparatus 3510. Conversely, in at least some alternate exemplary embodiments, the receiver/stimulator is configured to simply pass on data indicative of the signal that is received, or the fact that no signal is received (which can simply be no output of a signal from the receiver/stimulator) via link 3510 to test apparatus 3510. That is, in this regard, the cochlear implant 100 serves simply to generate the requisite electrical signals to be sent to the electrodes, under the instructions of the test apparatus 3510, and to output a signal via the link 3520 to the test apparatus 3510 indicating the response to those outputted signals.

Note further, that in an exemplary embodiment, the test apparatus 3510 could be part of the system 400. In an exemplary embodiment, the test apparatus 3510 can be located within the packaging 410 along with the cochlear implant 100. The inductance coil of the test apparatus 3510 can be located proximate to and/or juxtaposed with the inductance coil of the receiver/stimulator of the cochlear implant 100 (just as can be the case during testing with the test apparatus 3510 outside the packaging 410, except that the packaging material 410 is not present between the two coils). Indicators can be present on the test apparatus 3510 that indicate whether or not there exists the presence of an open circuit and/or a short circuit where one should not be. In an exemplary embodiment, this can be done via the use of LEDs, etc.

Note further that in an exemplary embodiment, the cochlear implant 100 itself can be configured to test itself (providing that the features of the system 400 are present), and provide its own indication of whether there exists an open circuit and/or a short circuit where one should not exist. In an exemplary embodiment, the receiver/stimulator can include an input output interface component that can enable a user to initiate the testing and/or conveyed to the user data regarding the results of the test. By way of example only and not by way limitation, an LED can flash a certain color and/or with a certain pattern to convey data as to whether or not there exists an open circuit and/or a short circuit where one should not exist.

Any arrangement that can enable the teachings detailed herein and/or variations thereof to be practiced can be utilized in at least some embodiments.

It is noted that various electrical properties can be utilized to practice the teachings detailed herein. By way of example only and not by way limitation, conductive elements of a known capacitance can be located between and in contact with two or more electrodes, and testing for an open circuit and/or a short circuit can be executed utilizing electrical engineering principles in view of the known capacitance of the conductor located between two or more electrodes. Still further by way of example only and not by way limitation, conductive elements with a known resistance can be located between and in contact with two or more electrodes, and testing for an open circuit and/or a short circuit can be executed utilizing electrical engineering principles in view of the known resistance of the conductor located between the two or more electrodes.

It is noted that any disclosure herein with respect to testing for an open circuit also corresponds to a disclosure of also testing for a short circuit before or after testing for the open circuit and/or simultaneously with testing for the open circuit.

As noted above, some and/or all of the teachings detailed herein can be used with a hearing prosthesis, such as a cochlear implant. That said, while the embodiments detailed herein have been directed towards cochlear implants, other embodiments can be directed towards application in other types of hearing prostheses, such as by way of example, other types of electrode arrays used in medical devices (e.g., pacemakers, nerve stimulators, etc.). Indeed, embodiments can be utilized with any type of medical device that utilizes an implanted electrode array, or even a non-implanted array, at least if there is utilitarian value with respect to conducting a test for an open circuit while the electrode array is located within packaging.

It is noted that any disclosure with respect to one or more embodiments detailed herein can be practiced in combination with any other disclosure with respect to one or more other embodiments detailed herein.

It is noted that some embodiments include a method of utilizing a system 400 having one or more or all of the teachings detailed herein and/or variations thereof. In this regard, it is noted that any disclosure of a device and/or system herein also corresponds to a disclosure of utilizing the device and/or system detailed herein, at least in a manner to exploit the functionality thereof. Further, it is noted that any disclosure of a method of manufacturing corresponds to a disclosure of a device and/or system resulting from that method of manufacturing. It is also noted that any disclosure of a device and/or system herein corresponds to a disclosure of manufacturing that device and/or system. Moreover, any disclosure of a method action herein also corresponds to a system and/or a device for executing that method action. In this regard, in an exemplary embodiment, there is an apparatus 400 that is configured so as to enable any one or more of the method actions detailed herein.

While various embodiments have been described above, it should be understood that they have been presented by way of example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the following claims and their equivalents.

What is claimed is:

1. An apparatus, comprising:
a sterilely sealed package; and
an electrode assembly sterilely sealed in the package, wherein the apparatus is configured to enable testing, with a conductive material, for an open circuit between two electrodes of the electrode assembly with the electrode assembly sterilely sealed in the package, wherein
the apparatus is configured to disable the enablement of the testing for the open circuit while the electrode assembly is sterilely sealed in the package.

2. The apparatus of claim 1, wherein:
the electrode assembly is in a state prepared for direct implantation into a recipient upon opening of the package.

3. The apparatus of claim 2, wherein at least one of:
the apparatus includes components separate from the package within the package that envelope the two electrodes that are configured to enable the testing for the open circuit; or
the apparatus includes components that are integral to the package that are configured to establish a conductive path between the two electrodes to enable the testing for the open circuit.

4. The apparatus of claim 1, wherein:
the apparatus provides conductivity between two electrodes of the electrode assembly sufficient to enable testing for an open circuit between the two electrodes while also enabling testing for a short circuit between the two electrodes with the conductivity present between the two electrodes.

5. The apparatus of claim 4, wherein the apparatus includes an electrically conductive foam portion that directly contacts the two electrodes.

6. The apparatus of claim 1, wherein at least a portion of the package is made of the conductive material and is in direct contact with electrodes of the electrode assembly.

7. A method, comprising:
obtaining an electrode array within a sealed package sterilely isolated from an external environment thereof;
testing, with a conductive material, for an open circuit between two electrodes of the electrode array while the electrode array is sterilely isolated from the external environment within the sealed package; and
testing for a short circuit in the electrode array while the electrode array is sterilely isolated from the external environment within the sealed package.

8. The method of claim 7, further comprising:
eliminating the sterile isolation after testing and implanting the electrode array in a human recipient.

9. The method of claim 8, wherein:
the action of implanting the electrode array includes implanting the electrode array into the human recipient after eliminating the sterile isolation without adding material to or removing material from the electrode array.

10. The method of claim 8, wherein:
the action of testing for an open circuit includes testing for the open circuit while the recipient is under anesthesia and prepared for implantation; and the method further includes determining whether to implant the electrode array in the recipient based on the testing.

11. The method of claim 7, further comprising:
manipulating package material forming the sterile isolation from a first state to a second state and subsequently testing for one of the open circuit or the short of the electrode array while the electrode array is sterilely isolated from the external environment.

12. The method of claim 11, further comprising:
testing for the other of the open circuit or the short circuit while the package material is in the first state.

13. The method of claim 7, wherein:
the action of testing is executed during storage.

14. The method of claim 7, wherein:
the action of testing for an open circuit is executed by establishing a conductive path of solid material between the two electrodes.

15. The method of claim 14, wherein:
the solid is a solid other than foam.

16. The method of claim 15, wherein:
the solid material is in the form of a body that includes a discrete passageway therein that establishes the conductive path.

17. The method of claim 7, wherein:
the action of testing is executed immediately after packaging and immediately prior to implantation of the electrode array into a recipient.

18. The method of claim 7, wherein the action of testing for an open circuit includes utilizing the package which is made of the conductive material and is in direct contact with the two electrodes of the electrode assembly to provide a conductive path between the two.

19. The method of claim 7, wherein:
the method further comprises opening the package;
the electrode array is stored in the sterile environment established by the package until the package is opened.

20. An apparatus, comprising:
a package; and
an electrode array sterilely sealed in the package, wherein the apparatus is configured to provide electrical conductivity between two electrodes of the electrode array with a conductive material, wherein at least one of:
the apparatus is configured to alternately provide and eliminate the electrical conductivity between the two electrodes, with the conductive material, while sterilely sealed in the package; or
the apparatus is configured to vary an impedance between electrodes of the electrode array from more than 1000 ohms to less than 100 ohms, with the conductive material, while sterilely sealed in the package.

21. The apparatus of claim 20, wherein:
the apparatus is configured to alternately provide and eliminate the electrical conductivity between the two electrodes, with the conductive material, while sterilely sealed in the package.

22. The apparatus of claim 20, wherein:
the apparatus is configured to vary an impedance between electrodes of the electrode array from more than 1000 ohms to less than 100 ohms, with the conductive material, while sterilely sealed in the package.

23. The apparatus of claim 22, wherein:
the apparatus is configured to vary the impedance via magnetic manipulation of a component within the package by a magnetic field extending through the package.

24. The apparatus of claim 20, wherein:
the package includes a foam portion that provides the electrical conductivity.

25. The apparatus of claim 20, wherein:
the apparatus is configured to controllably initiate the establishment of the electrical conductivity between the two electrodes via material completely within the package that is also sterilely sealed in the package.

26. The apparatus of claim 20, wherein:
the apparatus is configured to have the electrical conductivity between the two electrodes at all times while the electrode array is sterilely sealed in the package.

27. A system, comprising:
a package; and
a cochlear implant comprising an electrode array and a receiver-stimulator sealed within the package, wherein the system is configured to enable open circuit testing with a conductive material and short circuit testing of the electrode array while the electrode array is sealed in the package.

28. The system of claim 27, wherein:
the electrode array is a curved electrode array in a curved orientation.

29. The system of claim 28, wherein:
the electrode array is curved to subtend an angle of at least 360 degrees.

30. The system of claim 27, wherein:
the electrode array includes recessed electrodes.

31. The system of claim 27, wherein:
the electrode array is sterilely sealed within the package, and wherein the electrode array includes a plurality of electrodes and a plurality of leads.

32. The system of claim 27, wherein:
the package is heat sealed to establish a completely sterilely sealed package, thereby sterilely sealing the cochlear implant in the package.

* * * * *